US010769244B2

(12) United States Patent
Degen et al.

(10) Patent No.: US 10,769,244 B2
(45) Date of Patent: Sep. 8, 2020

(54) SYSTEMS AND METHODS FOR MANAGING AND ANALYZING DATA GENERATED BY AN IMPLANTABLE DEVICE

(71) Applicant: Sequana Medical NV, Zwijnaarde (BE)

(72) Inventors: Thomas Werner Degen, Birmensdorft (CH); Stefan Tschumper, Wattwil (CH)

(73) Assignee: Sequana Medical NV, Zwijnaarde (DE)

( * ) Notice: Subject to any disclaimer, the term of this patent is extended or adjusted under 35 U.S.C. 154(b) by 171 days.

(21) Appl. No.: 15/684,479

(22) Filed: Aug. 23, 2017

(65) Prior Publication Data
US 2018/0060520 A1 Mar. 1, 2018

Related U.S. Application Data

(60) Provisional application No. 62/380,284, filed on Aug. 26, 2016.

(51) Int. Cl.
G06F 19/00 (2018.01)
A61B 5/00 (2006.01)
(Continued)

(52) U.S. Cl.
CPC ........ *G06F 19/3418* (2013.01); *A61B 5/0006* (2013.01); *A61B 5/0022* (2013.01);
(Continued)

(58) Field of Classification Search
CPC . G06F 19/3418; A61B 5/0006; A61B 5/0022; A61B 5/02055; A61B 5/0402; A61B 5/07; A61B 5/6847; A61B 5/746
(Continued)

(56) References Cited

U.S. PATENT DOCUMENTS 3,540,451 A 11/1970 Zenman
3,575,158 A 4/1971 Summers
(Continued)

FOREIGN PATENT DOCUMENTS

CN 101485683 A 7/2009
CN 201930383 U 8/2011
(Continued)

OTHER PUBLICATIONS

"Pump implant for cancer patients 'is a game-changer' for thousands", The Times, Health News, p. 11, Jan. 18, 2013.
(Continued)

Primary Examiner — Christopher A Flory
(74) Attorney, Agent, or Firm — Eversheds Sutherland (US) LLP; Christopher C. Bolten; Nicola A. Pisano

(57) ABSTRACT

A system is provided including an implantable device configured to be implanted subcutaneously within a patient, a clinician monitoring and control device, an optional patient mobile device, a remote server and/or at least one data analyst device used by a data analyst. The implantable device may communicate with any or all of the monitoring and control device, the mobile device and/or the remote server through the charging device or by establishing a direct wireless connection with each such device. The data analyst device may establish a direct connection with the remote server and also may establish a connection with the monitoring and control device and the mobile device. By analyzing and reviewing the data generated by the implantable device, the data analyst may diagnose a medical condition or indicate a heightened risk of a condition.

19 Claims, 9 Drawing Sheets

(51) Int. Cl.

| | | |
|---|---|---|
| *A61B 5/0205* | (2006.01) | |
| *A61B 5/0402* | (2006.01) | |
| *A61B 5/07* | (2006.01) | |
| *A61M 27/00* | (2006.01) | |
| *G16H 10/60* | (2018.01) | |
| *G16H 50/30* | (2018.01) | |
| *G16H 50/20* | (2018.01) | |
| *A61B 5/024* | (2006.01) | |
| *A61B 5/08* | (2006.01) | |

(52) U.S. Cl.
CPC ........ *A61B 5/02055* (2013.01); *A61B 5/0402* (2013.01); *A61B 5/07* (2013.01); *A61B 5/6847* (2013.01); *A61B 5/746* (2013.01); *A61M 27/002* (2013.01); *A61B 5/02444* (2013.01); *A61B 5/08* (2013.01); *A61M 2205/18* (2013.01); *A61M 2205/3334* (2013.01); *A61M 2205/3365* (2013.01); *A61M 2205/3368* (2013.01); *A61M 2205/3523* (2013.01); *G16H 10/60* (2018.01); *G16H 50/20* (2018.01); *G16H 50/30* (2018.01)

(58) Field of Classification Search
USPC .................................................. 600/300, 301
See application file for complete search history.

(56) References Cited

U.S. PATENT DOCUMENTS

| | | |
|---|---|---|
| 3,654,932 A | 4/1972 | Newkirk et al. |
| 3,810,259 A | 5/1974 | Summers |
| 3,910,283 A | 10/1975 | Leveen |
| 4,014,346 A | 3/1977 | Brownlee et al. |
| 4,083,786 A | 4/1978 | Tsuda et al. |
| 4,240,434 A | 12/1980 | Newkirk |
| 4,261,341 A | 4/1981 | Hakim et al. |
| 4,354,933 A | 10/1982 | Lester |
| 4,416,657 A | 11/1983 | Berglund |
| 4,419,094 A | 12/1983 | Patel |
| 4,475,898 A | 10/1984 | Brodner et al. |
| 4,475,899 A | 10/1984 | Muller |
| 4,490,137 A | 12/1984 | Moukheibir |
| 4,553,956 A | 11/1985 | Muller |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,632,435 A | 12/1986 | Polyak |
| 4,657,530 A | 4/1987 | Buchwald et al. |
| 4,687,471 A | 8/1987 | Twardowski et al. |
| 4,725,207 A | 2/1988 | Buchwald et al. |
| 4,772,257 A | 9/1988 | Hakim et al. |
| 4,779,614 A | 10/1988 | Moise |
| 4,784,638 A | 11/1988 | Ghajar et al. |
| 4,850,955 A | 7/1989 | Newkirk et al. |
| 4,880,414 A | 11/1989 | Whipple |
| 4,904,236 A | 2/1990 | Redmont et al. |
| 4,963,129 A | 10/1990 | Rusch |
| 4,963,133 A | 10/1990 | Whipple |
| 5,011,472 A | 4/1991 | Aebischer et al. |
| 5,021,048 A | 6/1991 | Buckholtz |
| 5,037,385 A | 8/1991 | O'Byrne |
| 5,057,075 A | 10/1991 | Moncrief et al. |
| 5,071,408 A | 12/1991 | Ahmed et al. |
| 5,078,688 A | 1/1992 | Lobodzinski et al. |
| 5,147,281 A | 9/1992 | Thornton et al. |
| 5,167,615 A | 12/1992 | East et al. |
| 5,180,387 A | 1/1993 | Ghajar et al. |
| 5,254,084 A | 10/1993 | Geary |
| 5,356,386 A | 10/1994 | Goldberg et al. |
| 5,385,541 A | 1/1995 | Kirsch et al. |
| 5,387,188 A | 2/1995 | Watson |
| 5,387,192 A | 2/1995 | Glantz et al. |
| 5,391,143 A | 2/1995 | Kensey |
| 5,395,350 A | 3/1995 | Summers |
| 5,397,354 A | 3/1995 | Wilk et al. |
| 5,472,323 A | 12/1995 | Hirabayashi et al. |
| 5,474,683 A | 12/1995 | Bryant et al. |
| 5,575,770 A | 11/1996 | Melsky et al. |
| 5,589,197 A | 12/1996 | Shockley et al. |
| 5,629,025 A | 5/1997 | Shockley et al. |
| 5,631,025 A | 5/1997 | Shockley et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,944,684 A | 8/1999 | Roberts et al. |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,405 A | 10/2000 | Nilsson et al. |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 * | 5/2005 | Tsukamoto .......... A61N 1/3787 320/107 |
| 6,905,474 B2 | 6/2005 | Borgesen |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,169,303 B2 | 1/2007 | Sullivan et al. |
| 7,195,608 B2 | 3/2007 | Burnett |
| 7,311,690 B2 | 12/2007 | Burnett |
| 7,335,179 B2 | 2/2008 | Burnett |
| 7,621,886 B2 | 11/2009 | Burnett |
| 7,670,332 B2 | 3/2010 | O'Keefe et al. |
| 7,909,790 B2 | 3/2011 | Burnett |
| 8,012,118 B2 | 9/2011 | Curtin et al. |
| 8,202,248 B2 | 6/2012 | Burnett et al. |

(56) References Cited

U.S. PATENT DOCUMENTS

| | | |
|---|---|---|
| 8,241,239 B2 | 8/2012 | Solomon et al. |
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,641,659 B2 * | 2/2014 | Soykan ............... A61M 1/284 604/27 |
| 8,771,221 B2 | 7/2014 | Burnett |
| 8,882,699 B2 | 11/2014 | Burnett |
| 8,961,448 B2 | 2/2015 | Forsell |
| 8,992,456 B1 | 3/2015 | Powell |
| 9,039,652 B2 * | 5/2015 | Degen .................. A61M 1/28 604/29 |
| 9,138,523 B2 | 9/2015 | Burnett et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,381,301 B2 | 7/2016 | Lattanzio et al. |
| 9,421,347 B2 | 8/2016 | Burnett |
| 9,577,459 B2 | 2/2017 | Degen et al. |
| 9,675,327 B2 | 6/2017 | Johnson et al. |
| 9,913,968 B2 | 3/2018 | Burnett |
| 9,956,336 B2 | 5/2018 | Degen et al. |
| 2002/0013545 A1 | 1/2002 | Soltanpour et al. |
| 2002/0022793 A1 | 2/2002 | Bertrand et al. |
| 2002/0123715 A1 | 9/2002 | Sorenson et al. |
| 2003/0114787 A1 | 6/2003 | Gura |
| 2003/0114898 A1 * | 6/2003 | Von Arx ................ A61N 1/08 607/60 |
| 2003/0163079 A1 | 8/2003 | Burnett |
| 2003/0171710 A1 * | 9/2003 | Bassuk .............. A61M 31/002 604/67 |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 * | 5/2004 | Forsell ............... A61F 2/0036 623/1.25 |
| 2004/0126775 A1 | 7/2004 | Altieri et al. |
| 2004/0147871 A1 | 7/2004 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |
| 2006/0036208 A1 * | 2/2006 | Burnett ............ A61M 5/14276 604/9 |
| 2006/0058731 A1 | 3/2006 | Burnett et al. |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0228071 A1 * | 10/2007 | Kamen ................ A61M 5/142 222/52 |
| 2007/0255345 A1 | 11/2007 | Krause |
| 2007/0299317 A1 | 12/2007 | Hoyme et al. |
| 2008/0024294 A1 * | 1/2008 | Mazar .................... H04K 3/41 340/539.12 |
| 2008/0108935 A1 | 5/2008 | Nyhart, Jr. |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0222065 A1 * | 9/2009 | Dlugos, Jr. .............. A61B 5/03 607/60 |
| 2009/0275805 A1 * | 11/2009 | Lane ..................... A61B 5/01 600/300 |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0022902 A1 * | 1/2010 | Lee .................... A61B 5/0006 600/509 |
| 2010/0114012 A1 | 5/2010 | Sandford et al. |
| 2010/0185225 A1 * | 7/2010 | Albrecht ............... A61B 5/036 606/191 |
| 2010/0215375 A1 | 8/2010 | Reams |
| 2010/0222846 A1 * | 9/2010 | Goetz ................. G06F 19/3418 607/59 |
| 2010/0234793 A1 | 9/2010 | Dacey, Jr. et al. |
| 2010/0249692 A1 * | 9/2010 | Dacey, Jr. ............. A61L 2/0011 604/9 |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0172545 A1 * | 7/2011 | Grudic .................. A61B 5/021 600/485 |
| 2011/0184339 A1 | 7/2011 | Tan |
| 2011/0184340 A1 | 7/2011 | Tan et al. |
| 2011/0202041 A1 * | 8/2011 | Forsell .................. A61F 2/0036 604/891.1 |
| 2011/0291613 A1 | 12/2011 | Rosik et al. |
| 2012/0035255 A1 | 2/2012 | Schatz et al. |
| 2012/0041279 A1 * | 2/2012 | Freeman ............... A61B 5/0205 600/301 |
| 2012/0209085 A1 * | 8/2012 | Degen ................... A61M 1/28 600/301 |
| 2012/0209165 A1 * | 8/2012 | Degen ................... A61M 1/28 604/9 |
| 2012/0235503 A1 * | 9/2012 | Kesler ..................... H03H 7/40 307/104 |
| 2012/0235634 A1 * | 9/2012 | Hall ........................ H03H 7/40 320/108 |
| 2013/0199998 A1 | 8/2013 | Kelly et al. |
| 2013/0211322 A1 * | 8/2013 | Degen ................... A61M 1/285 604/29 |
| 2013/0289334 A1 * | 10/2013 | Badstibner ............ A61M 1/127 600/16 |
| 2013/0303971 A1 | 11/2013 | Budgett et al. |
| 2014/0005743 A1 * | 1/2014 | Giuffrida ........... A61N 1/36135 607/45 |
| 2014/0012180 A1 | 1/2014 | Levin et al. |
| 2014/0066841 A1 * | 3/2014 | Degen .................. A61M 1/285 604/28 |
| 2014/0074180 A1 * | 3/2014 | Heldman ............... A61B 5/1101 607/45 |
| 2014/0098627 A1 | 4/2014 | Mochizuki |
| 2014/0200481 A1 * | 7/2014 | Johnson ............ A61M 5/14236 600/561 |
| 2014/0266022 A1 * | 9/2014 | Degen ..................... H02J 7/007 320/108 |
| 2014/0275727 A1 * | 9/2014 | Bonde ................. A61M 1/1086 600/17 |
| 2014/0275827 A1 * | 9/2014 | Gill ....................... A61B 5/4848 600/301 |
| 2015/0088090 A1 | 3/2015 | Macy, Jr. |
| 2016/0000984 A1 | 1/2016 | Burnett et al. |
| 2016/0022971 A1 | 1/2016 | Degen et al. |
| 2016/0087687 A1 * | 3/2016 | Kesler ................. H04B 5/0037 307/104 |
| 2016/0151553 A1 * | 6/2016 | Bonde ................. A61M 1/1086 600/17 |
| 2016/0183819 A1 * | 6/2016 | Burnett ................ A61B 5/6853 600/309 |
| 2016/0303313 A1 * | 10/2016 | Burke .................... G16H 20/17 |
| 2016/0331947 A1 | 11/2016 | Burnett |
| 2017/0079760 A1 * | 3/2017 | Newman ............... A61F 2/004 |
| 2017/0128654 A1 | 5/2017 | Feld |
| 2017/0136221 A1 | 5/2017 | Budgett et al. |
| 2017/0173262 A1 * | 6/2017 | Veltz ................... A61M 5/1723 |
| 2017/0281848 A1 | 10/2017 | Axelsson et al. |
| 2018/0056050 A1 | 3/2018 | Degen et al. |
| 2018/0060520 A1 | 3/2018 | Degen et al. |
| 2018/0344917 A1 | 12/2018 | Inhaber |

FOREIGN PATENT DOCUMENTS

| | | |
|---|---|---|
| EP | 0 366 389 A2 | 5/1990 |
| EP | 0 980 685 | 2/2000 |

(56) References Cited

FOREIGN PATENT DOCUMENTS

| | | |
|---|---|---|
| EP | 1 362 605 A1 | 11/2003 |
| EP | 1 517 718 B1 | 3/2005 |
| EP | 1 539 294 B1 | 6/2005 |
| EP | 2 244 667 A1 | 11/2010 |
| EP | 2 676 638 B1 | 12/2013 |
| GB | 2 350 794 A | 12/2000 |
| JP | H04-327857 | 11/1992 |
| JP | 2000-072658 A | 3/2000 |
| JP | A2004-513681 | 5/2004 |
| JP | A2005-171892 | 6/2005 |
| WO | WO-97/41799 | 11/1997 |
| WO | WO-98/16171 | 4/1998 |
| WO | WO-99/34116 A1 | 7/1999 |
| WO | WO-02/07596 A1 | 1/2001 |
| WO | WO-03/072166 A1 | 9/2003 |
| WO | WO-2004/012806 A1 | 2/2004 |
| WO | WO-2004/105730 A1 | 12/2004 |
| WO | WO-2005/018708 A2 | 3/2005 |
| WO | WO-2006/023589 A2 | 3/2006 |
| WO | WO-2008/055248 A1 | 5/2008 |
| WO | WO-2009/091267 A2 | 7/2009 |
| WO | WO-2009/096854 A1 | 8/2009 |
| WO | WO-2010/077851 A2 | 7/2010 |
| WO | WO-2012/112664 A1 | 8/2012 |
| WO | WO-2013/122580 A1 | 8/2013 |
| WO | WO-2013/166038 A2 | 11/2013 |
| WO | WO-2014/140277 A1 | 9/2014 |
| WO | WO-2015/108782 A1 | 7/2015 |
| WO | WO-2018/037359 A1 | 3/2018 |

OTHER PUBLICATIONS

Bellot, Pablo, et al., Automated low flow pump system for the treatment of refractory ascites: A multi-center safety and efficacy study, Journal of Hepatology, 58(5):922-927 (2013).
Fukuda, et al., Survivin, a cancer target with an emerging role in normal adult tissues, Mol. Cancer Ther., 5(5):1087-1098 (2006).
International Search Report and Written Opinion dated Apr. 16, 2015 in Int'l PCT Patent Appl. No. PCT/US2015/010840.
Medtronic Reveal Ling™ LNQ11, Insertable Cardiac Monitor, Clinician Manual, 98 pages (2015).
Rosenblit et al., "Peritoneal-urinary drainage for treatment of refractory ascites: a pilot study," J. Vascular & Interv. Radiology, 9(6):998-1005 (Nov./Dec. 1998).
www.medtronic.com/us-en/patients/treatments-therapies/fainting-heart-monitor/reveal-linq-icm.html (May 2017) (Accessed Nov. 27, 2017).
Costanzo et al., "Early Ultrafiltration in Patients with Decompensated Heart Failure and Diuretic Resistance," J. Am. Coll. Cardiol., 46(11):2047-2051 (2005).
Doty, et al., Effect of Increased Renal Venous Pressure on Renal Function, J. Trauma., 47(6):1000-3 (1999).
Francois, et al., Peritoneal Dialysis for Chronic Congestive Heart Failure, Blood Purif., 40(1):45-52 (2015).
Hecking, et al., Sodium Setpoint and Sodium Gradient: Influence on Plasma Sodium Change and Weight Gain, Am J. Nephrol, 33(1):39-48 (2011).
Houlberg et al., "Terminal Right Heart Failure Due to Complex Congenital Cardiac Disease Successfully Managed by Home Peritoneal Drainage," Cardiol. Young, 13(6):568-70 (2003).
International Search Report & Written Opinion dated Jan. 4, 2018 in Int'l PCT Patent Appl. Serial No. PCT/IB2017/055092.
International Search Report & Written Opinion dated Mar. 18, 2013 in Int'l PCT Patent Appl. Serial No. PCT/US2012/025188.
Kenny, Intra-Abdominal Pressure and Renal Function: The Venous Side of the Road, PulmCCM, Critical Carer, GI and Nutrition, Jul. 14, 2016, accessed on line on Mar. 27, 2017 at http://pulmccm.org/main/2016/critical-care-review/intra-abdominal-pressure-renal-function/.
McCausland, et al., Dialysate Sodium, Serum Sodium and Mortality in Maintenance Hemodialysis, 27(4):1613-1618 (2012).
Munoz Mendoza, et al., Dialysate sodium and sodium gradient in maintenance hemodialysis: a neglected sodium restriction approach? Nephrol Dial Transplant, 26(4):1281-1287 (2011).
Nakayama, et al., Clinical Effect of Low Na Concentration Dialysate (120mEq/L) for CAPD Patients, Abstracts of the XIII Annual CAPD Conference, Peritoneal Dialysis International, vol. 13, Supplement 1, 1993.
Ortiz et al., "Long-Term Automated Peritoneal Dialysis in Patients with Refractory Congestive Heart Failure," Advances in Peritoneal Dialysis, 19:77-80 (2003).
International Search Report dated Sep. 16, 2008 in Int'l PCT Patent Appl. Serial No. PCT/US2005/029305.
Puttagunta, et al., Peritoneal Dialysis for Heart Failure, Peritoneal Dialysis International, 35(6):645-649 (2015).
Rosenblit et al., "Peritoneal-Urinary Drainage for Treatment of Refractory Ascites: A Pilot Study," J. of Vascular & Interventional Radiology, 9(6):998-1005 (1998).
Ruhi, et al., Use of Peritoneal Ultrafiltration in the Elderly Refractory Congestive Heart Failure Patients, Int. Urol. and Nephrol., 44(3):963-969 (2012).
Zepeda-Orozco, et al., Dialysis Disequilibrium Syndrome, Pediatr. Nephrol, 27:2205-2211 (2012).
Communication Relating to the Results of the Partial International Search dated Dec. 8, 2017 in Int'l PCT Patent Appl. No. PCT/IB17/55093.
Extended European Search Report dated Sep. 18, 2019 in EP Patent Appl. Serial No. 19172235.4.

* cited by examiner

SYSTEMS AND METHODS FOR MANAGING AND ANALYZING DATA GENERATED BY AN IMPLANTABLE DEVICE

CROSS-REFERENCE TO RELATED APPLICATIONS

This application claims the benefit of the filing date of U.S. Provisional Patent Application No. 62/380,284 filed on Aug. 26, 2016, the disclosure of which is incorporated herein by reference.

TECHNICAL FIELD

The present disclosure relates generally to implantable medical devices and more specifically to managing and analyzing data generated by implantable medical devices.

BACKGROUND

Physiological data may offer medical experts an understanding of a person's wellbeing far beyond what may be gleaned by observation. For example, measuring a patient's temperature, pulse, pulse strength, respiratory rate, blood oxygen levels, tidal volume, blood pressure and various other physiological parameters may provide medical professionals a better understanding of the current state of a patient's body, vital organs and systems. Physiological data may further include measurements of biomarkers.

Physiological data also may provide early detection of a medical condition. As is the case with many medical conditions, early detection may be the difference between life and death. In the field of cancer, periodic monitoring of a patient's wellbeing may improve survival and decrease mortality by detecting cancer at an early stage when treatment is more effective. Similarly, early detection of heart disease allows the patient to change or eliminate habits that worsen their condition.

Even after a medical condition is detected, physiological data remains extremely valuable. By monitoring and analyzing a patient's symptoms and physiological measurements over an appropriate period of time, a better understanding of a patient's wellbeing or medical condition may be achieved. Monitoring a patient's symptoms and physiological measurements over a period of time will allow physicians and medical professionals to better understand the progression of the patient's medical condition and detect additional related and potentially unrelated conditions. Having a record of a patient's symptoms and physiological measurements provides an archive from which the significance and relevance of future changes may be determined.

Though physiological data may be gathered during hospital stays and office visits, the data gathered represents only glimpse into the patient's physiological wellbeing at that given period of time while the patient is in the hospital or doctor's office. With so few data points, it is difficult to truly understand how these physiological measurements are changing over time and how they relate to events and routines of a patient. Furthermore, the physiological measurements taken during a hospital stay or doctor's office visit are typically limited to non-invasive measurement mechanisms limited to the exterior of one's body. These types of measurements are often incapable of measuring interior parameters used as biomarkers such as temperature, pressure and other fluid parameters within a body cavity. Non-invasive measurements limited to the exterior of one's body typically do not serve as reliable biomarkers for conditions within the body.

Several devices have been produced that are directed to gathering specific physiological data outside of a hospital or doctor's office setting. Heart rate monitors are an example of a specific physiological measurement device used outside of the hospital setting. Heart rate monitors are typically worn by patients who have been diagnosed with a heart condition or have recently had a heart attack. Additionally, athletes are known to wear heart rate monitors for fitness purposes. Typically, heart rate monitors measure the heart rate from the exterior of the patient's body in a non-invasive manner. Some heart rate monitors are also capable of communicating to a mobile device allowing the user to view the data at a later time in a reader friendly way.

Similar in purpose is Medtronic's Reveal LINQ Insertable Cardiac Monitor device which continuously monitors a patient's heart and automatically detects and records abnormal heart rhythms. The system is implanted under the skin in the user's chest and continuously monitors a patient's heart activity in the form of an electrocardiogram (ECG). When a medical event occurs, an extracorporeal recording device is placed in close proximity to the implantable device to record the heart's rhythm during the medical episode.

Another device designed to gather specific physiological data outside of a hospital or doctor's office setting is Medtronic's Continuous Glucose Monitoring (CGM) system which measures glucose levels in real time and sends alerts to a remote monitor. The alerts include the direction glucose levels are going, early notification of oncoming lows and highs, alerts for lows or highs, and insights into how food, physical activity, medication, and illness impact glucose levels. The system consists of a glucose sensor inserted under the skin that measures glucose levels, a transmitter that sends the glucose information from the sensor to a monitor via wireless radio frequency, and a small external monitor that displays glucose levels on a screen and notifies the user if it detects that glucose is reaching a high or low limit.

While devices for measuring specific physiological parameters outside of the hospital or doctor's office setting have been developed and commercialized, these devices are only directed to measuring physiological parameters specific to the medical condition being treated or the part of the anatomy in question. Typically these devices are limited to one sensor, only measuring heart rate or glucose levels, for example. For this reason, any analysis of the data generated is often narrow in scope and directed to the medical condition being treated. While the limited data generated is helpful for better understanding that particular medical condition, it offers little to no insight into the body's overall wellbeing and how other parts of the body or systems within the body relate to the medical condition or part of the anatomy in question and therefore is often insufficient to serve as a biomarker.

Another drawback of these devices is that the monitoring or recording elements of the device are typically physically coupled to the sensing device or required to be in very close proximity to the sensing device. Where the sensing device is physically connected to the monitoring or recording element, this often requires a cable running transcutaneously from an implanted sensor to an external monitoring or recording device. The transcutaneous cable is not only painful but also could lead to infection. Additionally, the transcutaneous cable may restrict movement and hinder the user's daily activities.

In U.S. Pat. No. 9,039,652 to Degen, entitled apparatus and methods for treating intracorporeal fluid accumulation, incorporated by reference herein in its entirety, an implantable medical sensing device is configured to generate data and a charging device is configured to download the data. The implantable device disclosed in the Degen patent includes a mechanical gear pump that is configured to be coupled to the bladder and another cavity such as the peritoneal cavity. The implantable device in Degen further describes a plurality of sensors to continually monitor pressure, temperature, humidity, charge status, pump status, patient movement and other environmental and system related parameters. The plurality of sensors may communicate wirelessly with the charging device only when in close proximity. The charging device may then relay this information to a physician's computer.

Devices generally require that the monitoring or recording device be in close proximity to an implantable device. Considering that the implantable device will frequently be out of range of the monitoring and recording device, data may not be uploaded to the monitoring or recording device continuously. Accordingly, the implantable sensing device is required to include complex circuitry and memory for storing data between uploads.

Yet another drawback of these devices is that they often do not generate operational parameters to track the performance of the implanted machinery, such as an insulin pump. For example, while a Continuous Glucose Monitoring system may generate data regarding the patient's glucose levels, such systems do not measure insulin pump parameters, leaving the performance of the pump in question. Such data, if available, could be compared to the performance of the insulin pump to better optimize and understand the pump's effect on the body.

In view of the above-noted drawbacks of previously-known systems, it would be desirable to provide methods and systems for managing and analyzing physiological and operational data generated by an implantable device using a number of other computing devices not necessarily located in close proximity to the implantable device.

SUMMARY

The present disclosure overcomes the drawbacks of the previously-known systems having an implantable medical device by providing systems and methods for managing, reviewing and analyzing data generated by an implantable device configured to communicate wirelessly with a variety of communication devices including a remote data analyst device.

In accordance with the principles of the present invention, an exemplary system may include an implantable device to be implanted into a patient, a charging device for charging and/or communicating with the implantable device, a remote server configured to communicate with the implantable device and/or the charging device, a monitoring and control device and optionally, a mobile device, each of which may be in communication with the implantable device, the charging device, and/or the remote server, as well as each other. The system may further include a data analyst device in communication with at least the remote server.

The implantable device may have a microprocessor, a communication unit, and a plurality of sensors. The implantable device may generate operational data and physiological data and extract biomarkers based on information sensed by one or more sensors of the plurality of sensors. The operational data and physiological data may be processed using the microprocessor and communicated to other devices within the system using the communication unit. The implantable device may communicate with other devices in the system through communications with the charging device. In this manner, the implantable device may communicate operational data and/or physiological data to the charging device and the charging device may then send the data to other devices in the system. In this same way, other devices in the system may send operational parameters and/or instructions to the implantable device by relaying that information through the charging device. The communication unit of the implantable device may communicate with the charging device using any number of well-known wireless communication technologies. The other devices within the system may communicate with the charging device using any number of well-known wireless or wired communication technologies.

Alternatively, the implantable device may communicate directly to other devices within the system, without relaying communications through the charging device, by communicating wirelessly with these other devices. For example, the monitoring and control device and/or a mobile device may receive physiological and/or operational data from the implantable device. Wireless communication may be enabled by any number of well-known wireless communication technologies. In this manner, the implantable device may communicate operational data and/or physiological data to the other devices within the system and similarly the other devices within the system may wirelessly communicate operational parameters and/or instructions to the implantable device.

Whether the charging device is used as a relay or the implantable device communicates directly with the other devices in the system using wireless technology, the remote server may receive physiological and/or operational data. The data analyst device may access and download operational data and/or physiological data including biomarker data from the remote server. The data analyst device may be configured to analyze operational and/or physiological data and generate analyst data. The analyst data may include trends in the data and may compare the operational and/or physiological data to past data received from that individual's implantable device and/or to data from other implantable devices. The data also may be compared to predetermined or calculated thresholds. The analyst data may be communicated to the remote server and saved on the remote server for retrieval by the charging device, the monitoring and control device and/or the mobile device. The data analyst device also may generate a warning message containing a medical diagnosis or indication of a high risk of a medical condition, for example, and communicate the warning message to the charging device, the monitoring and control device, and/or the mobile device.

The implantable device also or alternatively may be programmed to analyze the operational and/or physiological data including biomarker data. For example, the implantable device may compare operational and/or physiological data to predetermined thresholds programmed into the implantable device. If the operational and/or physiological data exceeds or is otherwise inconsistent with the predetermined threshold, the implantable device may communicate a warning message to one or more of the other devices in the system.

DETAILED DESCRIPTION

The system of the present disclosure includes systems and methods for monitoring and analyzing physiological and/or operational data generated by an implantable medical device. In addition to an implantable device, an exemplary system constructed in accordance with the principles of the present invention may include a charging device, a patient's mobile communication device, a physician's monitoring and control device, and one or more remote servers. The one or more remote servers further may be in communication with one or more data analyst devices for accessing the operational and/or physiological data from the remote server and analyzing the operational and/or physiological data. The system may be configured to alert the physician and/or the patient of a medical condition or operational anomaly based on analysis of the physiological and/or operational data.

Data generated by implantable medical devices may be analyzed to achieve several different objectives, depending on the user group or business model. One goal may be to improve outcomes for patients with chronic diseases by delivering actionable insights to patients thereby influencing their behavior. Another goal may be to reduce healthcare cost and improve quality of life by enabling home care through provision of safe technical solutions for self-administration and remote monitoring. Another objective may be to improve outcomes, and potentially life expectancy, by delivering actionable insights to physicians based on personalized trend recognition and prediction, enabling early interventions or preventive therapeutical measures. Data generated by implantable devices may also deliver actionable insights to pharmaceutical companies based on biomarkers.

Data generated by implantable medical devices further ensures authenticity as an implantable device with a unique identifier cannot easily be removed from a patient. The data can be trusted to originate from that specific patient unlike wearable sensors which can easily be swapped between patients. Authenticity may be an important factor for new business models evolving around medical data.

Figure 1:
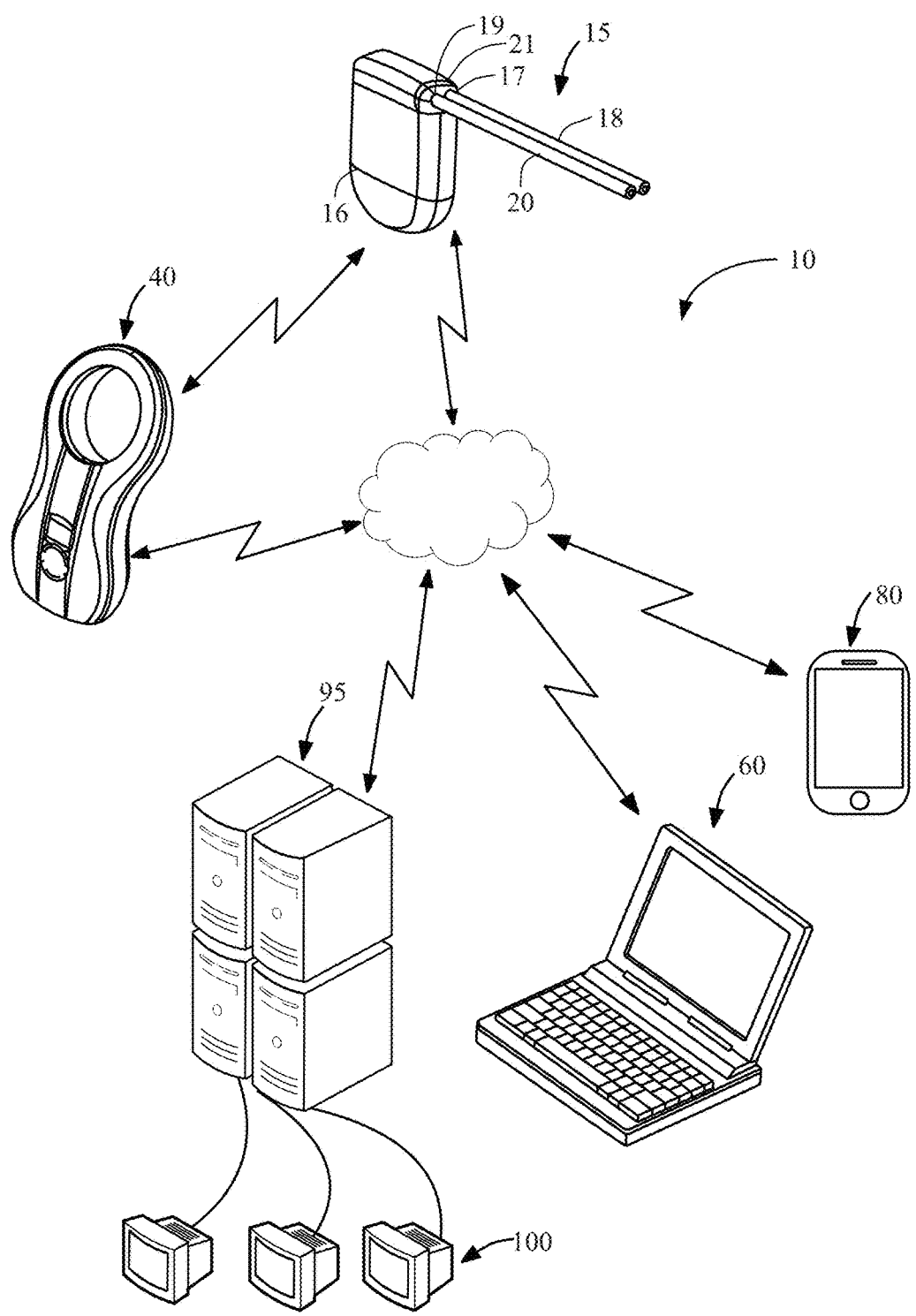
FIG. 1 illustrates an exemplary system of the present disclosure having an implantable device, a charging device.

Referring to FIG. 1, an overview of system 10 of the present disclosure is provided. System 10 may include implantable device 15, external charging device 40, monitoring and control device 60, mobile device 80 and remote server 95 as well as data analyst device 100.

Implantable device 15 is implanted subcutaneously into the body of a patient and is configured to generate various physiological and/or operational data and communicate physiological and/or operational data to other devices within system 10. As shown in FIG. 1 and discussed in more detail below, implantable device 15 may have low volume sealed biocompatible housing 16 which may house a plurality of sensors for generating physiological and/or operational data and a transceiver for transmitting physiological and/or operational data between implantable device 15 and other devices within system 10.

Implantable device 15 further may include hardware for treating a medical condition subcutaneously such as a pump. Implantable device 15 may include inlet port 17 coupled to inlet catheter 18 and outlet port 19 coupled to outlet catheter 20. The pump may be an electromechanical pump designed to move fluid from one body cavity to another body cavity, e.g. a first body cavity to a second body cavity. For example, the electromechanical pump may be used for treating ascites by positioning inlet catheter 18 in a patient's peritoneal cavity and outlet catheter 20 through the wall of a patient's bladder. In this manner, the electromechanical pump may move fluid from the peritoneal cavity to the patient's bladder as disclosed in the Degen patent discussed above. It is understood that implantable device 15 alternatively or additionally may be include other hardware within the biocompatible housing.

Figure 2:
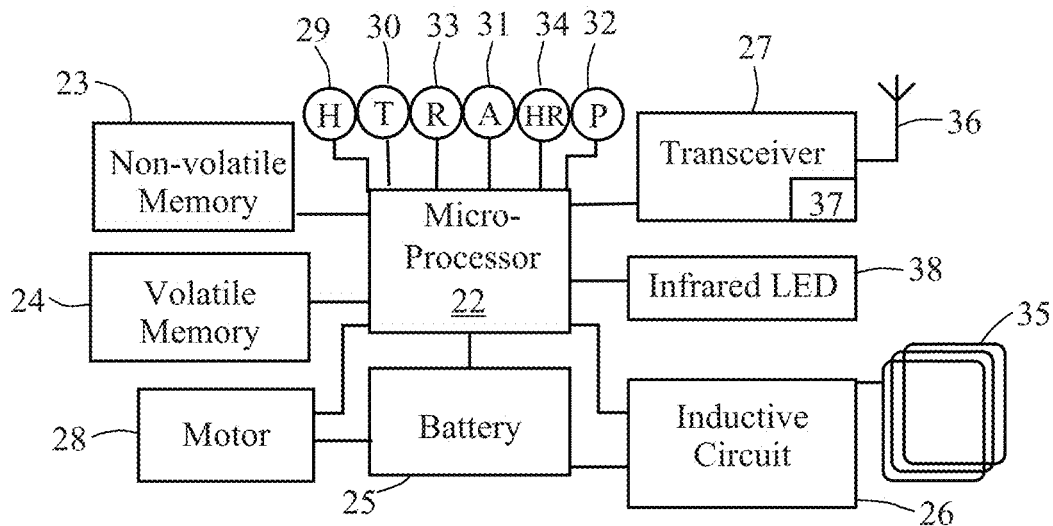
FIG. 2 is a schematic view of the electronic components of an exemplary embodiment of the implantable device.

Referring now to FIG. 2, exemplary functional blocks of implantable device 15 are illustrated. In particular, implantable device 15 may include control circuitry, illustratively microprocessor 22 coupled to nonvolatile memory 23, such as flash memory or electrically erasable programmable read only memory, and volatile memory 24 via data buses.

Microprocessor 22 may include firmware having instructions stored on non-transitory computer readable medium configured to cause transmission of operational data and/or physiological data to any or all of charging device 40, monitoring and control device 60, mobile device 80 and/or remote server 95. Instructions also may cause implantable device 15 to receive operational instructions. Microprocessor 22 may be electrically coupled to battery 25, inductive circuit 26, radio transceiver 27, electric motor 28, infrared LED 38 and a plurality of sensors, including for example, one or more humidity sensors 29, one or more temperature sensors 30, one or more accelerometers 31, one or more pressure sensors 32, one or more respiratory rate sensors 33 and one or more heart rate sensors 34. Other sensors additionally could be included in device 15, such as flow rate sensors, ECG sensors, pH sensors, and capacity sensors for measuring the amount of a liquid in a given cavity.

Operational data is indicative of the operation of implantable device 15 and/or hardware incorporated into implantable device 15 and may be generated by sensors incorporated into implantable device 15. Physiological data is indicative of the physiological state of the patient and also may be generated by sensors incorporated into system 10. For example, one or more humidity sensors 29 may be used to measure the humidity within the implantable device housing; one or more temperature sensors 30 may be used for measuring the temperature in one or more body cavities (e.g., peritoneal cavity, pleural cavity, pericardial cavity, and/or bladder) or region of the body (e.g., abdomen) and/or for measuring the temperature within implantable device 15 housing and/or the temperature of an implantable device component such as battery 25, one or more accelerometers 31 may be used for determining whether the patient is at rest and/or for sensing the position of a patient, e.g., vertical, horizontal; one or more pressure sensors 32 may be incorporated in implantable device 15 to measure blood pressure and/or the pressure within one or more body cavities (e.g., peritoneal cavity, pleural cavity, pericardial cavity, and/or bladder); one or more respiratory rate sensors 33 may be used to sense the number of breaths taken in a given period of time; and one or more heart rate sensors 34 may be used to sense the rate at which the heart is beating over a given period of time or the heart rate variation. Other sensors such as flow rate sensors, pH sensors and capacity sensors may be used for measuring the flow rate of the pump inlet and the pump outlet from which fluid viscosity may also be derived if the flow measurement is combined with pressure sensor measurements, the acidity of fluids within the body, and the degree to which a cavity is filled with fluid, respectively.

Examples of physiological data may include sensed data associated with the physiology of the patient such as temperature data associated with the one or more body cavities, accelerometer data associated with, for example, heart rate, respiratory rate and/or, pressure data associated with blood pressure and/or the one or more body cavities, respiratory rate data, and heart rate data, flow rate data associated with the one or more body cavities, pH data associated with bodily fluid pumped by the implantable device, and capacity data associated with the one or more body cavities. Physiological data may include biomarker data—measurable data indicative of a biological state or condition. For example, the viscosity of ascites in patients with liver disease may act as a biomarker indicative of an infection. Data gathered from multiple sensors within the patient may be combined to result in an effective biomarker. For example, temperature data in combination with ascites viscosity data may be combined to result an even more reliable indicator of an existing or developing infection. Examples of operational data may include data associated with the implantable device such as humidity data associated with the implantable device, temperature data associated with the implantable device, pressure data associated with the implantable device, flow rate data associated with the implantable device and may also include data related to the pump such as RPM data, efficiency data, run-time data, etc. In some cases, operational parameters may even serve as an indirect measurement of physiological parameters. For example, measurement of the motor torque of a pump can be used, in combination with other measured parameters, to determine fluid viscosity based on flow resistance.

Inductive circuit 26 may be electrically coupled to coil 35 to receive energy transmitted from charging device 40. Transceiver 27 may incorporate wireless communication unit 37 and may be coupled to antenna 36. Wireless communication unit 37 may be communication circuitry, such as a chipset, conforming to one or more wireless telephony/cellular standards such as GSM, LTE, CDMA, and/or other communication standards such as BLUETOOTH™, Bluetooth low energy, ZigBee, IEEE802.15, NFC, any IEEE 802.11 wireless standard such as Wi-Fi or Wi-Fi Direct or any other wireless standard comprising optical, acoustical or conductive intracorporal principles. All of the components depicted in FIG. 2 may be contained within housing 21, as shown in FIG. 1.

As shown in FIG. 1, charging device 40 may be a hand held device and having an ergonomic housing suitable for being held. As discussed in more detail, charging device 40 may transcutaneously transfer energy using inductive coils in the respective devices to charge battery 25 in implantable device 15. Charging device 40 also may be in direct communication with implantable device 15 using transceivers and communication units in each device. Charging device 40 may include non-transitory computer readable medium and instructions run on the non-transitory computer readable medium that permits communication with implantable device 15 including transmission of data to implantable device 15. The instructions also may permit charging device 40 to receive data from implantable device, monitoring and control device 60, mobile device 80 and data analyst device 100. Charging device 40 may communicate to implantable device 15 operational instructions, including at least operational parameters, and may receive from implantable device 15 physiological and/or operational data. Operational instructions may control the operation of implantable device 15 and hardware incorporated into implantable device 15. For example, operational instructions may instruct hardware incorporated into implantable device 15 to operate at specified operational parameters or settings. Operational parameters or settings may include pump displacement settings, pump voltage or current settings, pump flow rate settings, pump RPMs, or any other settings at which hardware incorporated into pump may be set to operate at. Charging device 40 may receive and store the physiological and/or operational data received from implantable device 15. Charging device 40 may further be in communication with other devices in system 10 such as monitoring and control device 60, mobile device 80 and remote server 95.

Figure 3:
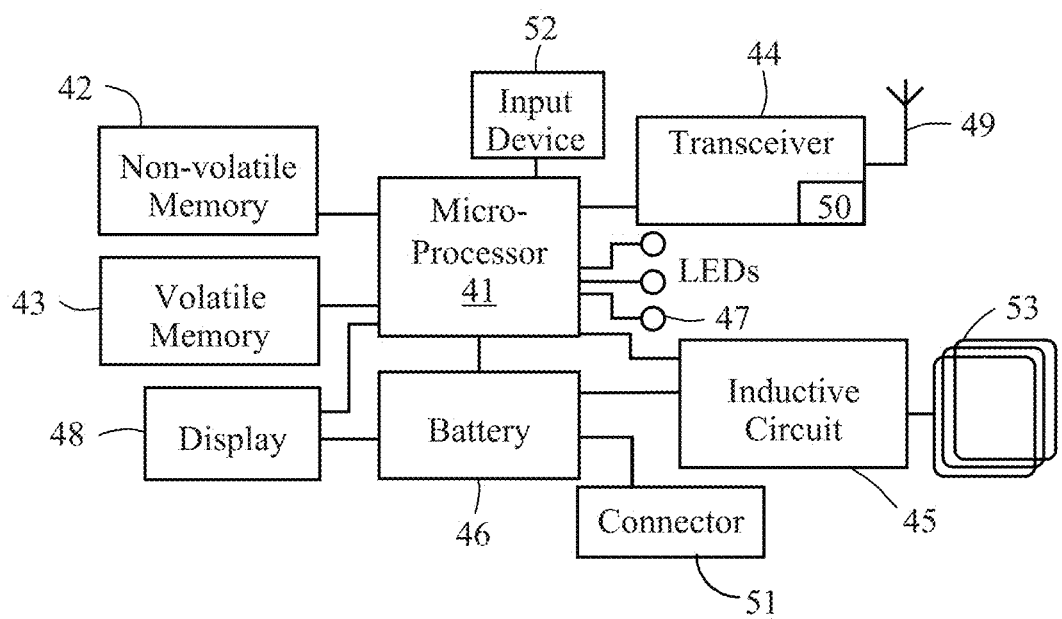
FIG. 3 is a schematic view of the electronic components of an exemplary embodiment of the charging device.

Referring now to FIG. 3, a schematic diagram of exemplary functional blocks of charging device 40 is described. Charging device 40 may include microprocessor 41 coupled to nonvolatile memory 42 (e.g., either EEPROM or flash memory), volatile memory 43, radio transceiver 44, inductive circuit 45, battery 46, indicator 47 and display 48. Microprocessor 41, non-volatile memory 42 and volatile memory 43, and radio transceiver 44 may be incorporated into a single unit, such as the MPS430 family of microprocessors, available from Texas Instruments Incorporated, Dallas, Tex. Transceiver 44 may be coupled to antenna 49 for sending and receiving information to and from implantable device 15. Transceiver 44 of charging device 40 may include wireless communication unit 50, that may be communication circuitry, such as a chipset, that conforms to one or more wireless telephony/cellular, BLUETOOTH™, Bluetooth low energy, ZigBee, IEEE 802.15, NFC, IEEE 802.11 wireless standards or any other wireless standard comprising optical, acoustical or conductive intracorporal principles, thereby enabling charging device 40 to communicate wirelessly with one or more of implantable device 15, monitoring and control system 60, mobile device 80 and remote server 95. It is further understood that wireless communication unit 50 may be compatible with more than one type of communication standard. Battery 46 may be coupled to connector 51 to charge battery 46 using an external power source. Input device 52, preferably a multi-function button, also may be coupled to microprocessor 41 to enable a patient to input a number of commands into charging device 40. Indicator 47 may comprise a plurality of LEDs that illuminate to indicate the quality of charge achieved between charging device 40 and implantable device 15, and therefore assist in optimizing the positioning of charging device 40 relative to implantable device 15 during recharging.

Microprocessor 41 also may execute firmware stored in nonvolatile memory 42 that controls communications and/or charging of the implantable device. Microprocessor 41 is configured to transfer and store data, such as physiological data, operational data, and/or event logs, uploaded to charging device 40 from implantable device 15. Microprocessor 41 may include firmware having instructions stored on non-transitory computer readable medium configured for receiving command inputs from monitoring control device 60 and/or mobile device 80 and for transmitting those command inputs to implantable device 15. Microprocessor 41 also may include firmware having instructions stored on non-transitory computer readable medium configured for transmitting command inputs to implantable device 15 using input device 52 incorporated into charging device 40. Microprocessor 41 also may include firmware having instructions stored on non-transitory computer readable medium configured to cause transmission of operational data and/or physiological data to remote server 95. The instructions also may cause communication unit 50 of charging device 40 to communicate with remote server 95 over the internet and/or over via a wireless telephony regime. Furthermore, the instructions may cause the communications between remote server 95 and charging device 40 to be encrypted. Microprocessor 41 may also control and monitor various power operations of charging device 40, including operation of inductive circuit 45 during recharging of the implantable device and displaying the state of the charge, e.g. the charge rate or percentage charged.

Inductive circuit 45 is coupled to coil 53, and is configured to inductively couple with coil 35 of implantable device 15 to recharge battery 25 of implantable device 15. Energy transfer is accomplished via electromagnetic coupling of coil 53 with coil 35 in the implantable device. As will be appreciated by one of ordinary skill, an alternating current may be delivered through coil 53, which causes an electromagnetic field to be established around coil 53, which induces an alternating current in coil 35 when coil 53 and 35 are held in close proximity.

Monitoring and control device 60, shown in FIG. 1, may be a clinician or physician computer used by the clinician or physician to, among other things, set and adjust operational parameters and download event logs as well as retrieve and display physiological and/or operational data generated by implantable device 15 as well analyst data generated by analyst device 65. Monitoring and control device 60 may be any computing device (e.g., personal computer, laptop, tablet, smartphone, etc.) of the clinician and is illustratively a laptop computer. Using monitoring and control device 60, a clinician may review data generated by implantable device 15 and track a patient's health in addition to the performance of hardware incorporated into implantable device 15. A clinician or physician using monitoring and control device 60 may also receive actionable insight and administer treatment or otherwise effectuate changes to improve the patient's condition or wellbeing.

Figure 4:
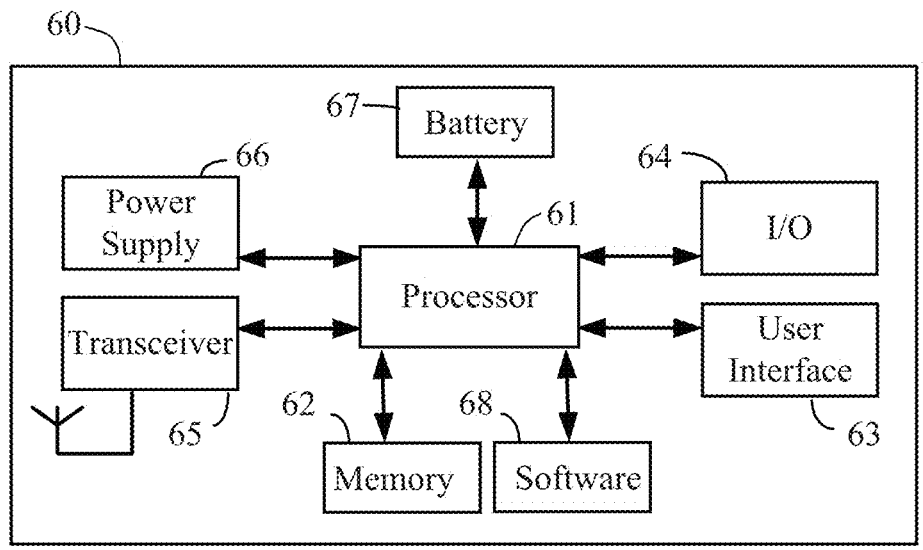
FIG. 4 is a schematic view of the electronic components of an exemplary embodiment of the monitoring and control device.

Referring now to FIG. 4, a schematic diagram of exemplary functional blocks of monitoring and control device 60 is described. Monitoring and control device 60 preferably includes components generally found on a conventional personal computing device, such as processor 61, volatile and/or non-volatile memory 62, user interface 63 such as digital display, input and output components 64 including, for example, a keyboard, a mouse and a USB port, transceiver 65, a power supply port 66, and a battery 67. Transceiver 65 may include wireless communication circuitry conforming to one or more of cellular, BLUETOOTH™, Bluetooth low energy and ZigBee standards, IEEE 802.15, NFC or any IEEE 802.11 wireless standard such as Wi-Fi or Wi-Fi Direct. Furthermore, monitoring and control device 60 may include software 68 that, when run on processor 61, retrieves and displays physiological and/or operational data and, when run on monitoring and control device 60, causes monitoring and control device 60 to communicate operational instructions, including operational parameters, to implantable device 15 and/or charging device 40. The physiological and/or operational data may be transmitted to monitoring and control device 60 from implantable device 15, charging device 40, remote server 95, and/or data analyst device 100.

As shown in FIG. 1, optional mobile device 80 also may be incorporated in system 10. Mobile device 80 may be a patient mobile communication device and may be used by the patient or a person assisting the patient to, among other things, view physiological and/or operational data. Mobile device 80 may be any mobile communication device (e.g., smartphone, tablet, smartwatch, laptop, etc.) of the user/patient/caregiver and is illustratively a smartphone having a large display. As discussed in more detail below, using mobile device 80, the patient may communicate with implantable device 15, charging device 40, and/or monitoring and control device 60.

Figure 5:
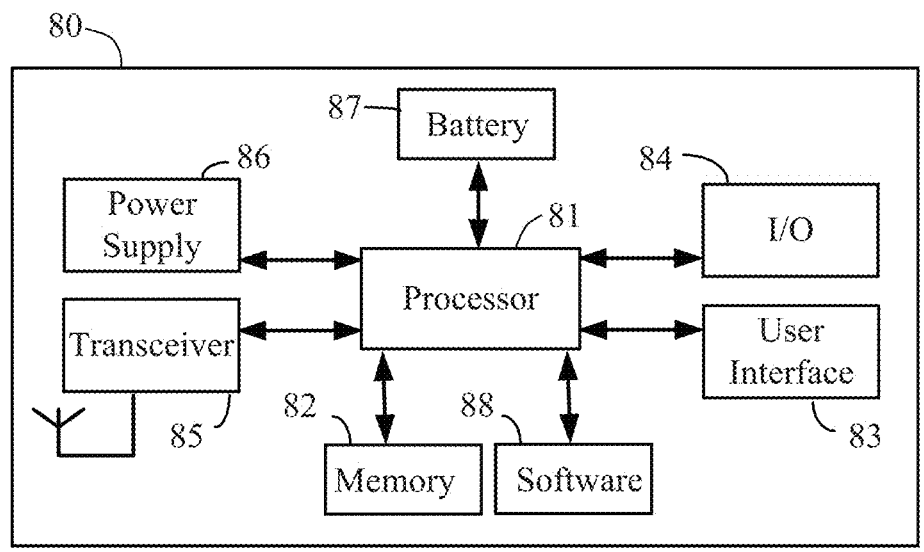
FIG. 5 is a schematic view of the electronic components of an exemplary embodiment of the mobile device.

Referring now to FIG. 5, a schematic diagram of exemplary functional blocks of mobile device 80 is described. Mobile device 80 may include components generally found on any modern mobile device such as processor 81, volatile and/or non-volatile memory 82, user interface 83 such as digital display, input and output mechanisms 84 including, for example, a keyboard, touchscreen or a USB port, transceiver 85, power supply port 86, and battery 87. Transceiver 85 may include a wireless communication circuitry conforming to one or more of cellular standards such as GSM, LTE, CDMA or other communication standards such as BLUETOOTH™, Bluetooth low energy, ZigBee, NFC, any IEEE 802.11 wireless standard such as Wi-Fi or Wi-Fi Direct. For example, transceiver 85 may conform to a cellular standard having SMS text and voice message capability. Furthermore, mobile device 80 may include software 88 having instructions stored on non-transitory computer readable medium that, when run on processor 81, causes mobile device 80 to communicate with implantable device 15 and/or remote server 95 to retrieve and display physiological data, operational data, and/or analyst data. Software 88 may further be configured to generate instructions that, when run by processor 81, cause mobile device 80 to communicate operational instructions to implantable device 15 and charging device 40.

Remote server 95, as shown in FIG. 1, may receive physiological and/or operational data generated by implantable device 15 and may store the physiological and/or operational data. Remote server 95 may be accessed for retrieval of the physiological and/or operational data as well as any other data generated by implantable device 15 or by other devices such as mobile device 80, monitoring and control device 60, and/or data analyst device 100. Remote server 95 may communicate with other devices in system 10 using any of the known methods of communication discussed above. For example, remote server 95 preferably is connected to the Internet to communicate with any or all of charging device 40, monitoring and control device 60, mobile device 80, and/or data analyst device 100.

Data analyst device 100, also shown in FIG. 1, may be used by a data analyst to compile, review and analyze the data generated by implantable device 15 and generate data analysis based on the data generated by implantable device 15. Data analyst device 100 may include a computer readable medium and instructions stored on the computer readable medium and run on data analyst device that cause the data analyst device to communicate with remote server 95 to receive from remote server 95 operational data and/or physiological data. Additionally, the instructions may cause data analyst device 100 to compile the operational and/or physiological data and generate analyst data. The instructions may also cause data analyst device 100 to communicate with remote server 95 to transmit analyst data to remote server 95. Data analyst device 100 may make a wired connection with remote server 95 via any suitable LAN or WAN or may communicate wirelessly with remote server 95. Using data analyst device 100, the data analysis generated by data analyst device 100 may be transmitted to the remote server 95 and stored on remote server 95 for retrieval by monitoring and control device 60 and/or mobile device 80.

Data analyst device 100 may be any computing device (e.g., personal computer, laptop, tablet, smartphones, etc.) of the data analyst configured to retrieve physiological and/or operational data and analyze the data for trends and anomalies. The instructions also may cause data analyst device to generate analyst data or aid the data analyst in the generation of analyst data which may include a diagnosis a medical condition and/or an indication a heightened risk of a medical condition. The instructions run on the non-transitory computer readable medium may cause data analyst device 100 to generate a warning message when the operational data and/or physiological data exceeds preprogrammed thresholds and also may cause data analyst device 100 to communicate the warning message to the patient mobile communication device 80 and/or monitoring and control device 60. Data analyst device 100 may include components generally found on a conventional personal computing device, such as a processor, volatile and/or non-volatile memory, a user interface such as digital display, a transceiver, a battery and input and output components such as a keyboard, a mouse and a USB port.

There are at least two ways in which implantable device 15 may communicate with system 10. First, implantable device 15 may be in direct wireless communication with charging device 40 using one or more of any well-known wireless standards such as GSM, LTE, CDMA, BLUETOOTH™, Bluetooth low energy, ZigBee, NFC, or any IEEE 802.11 wireless standard such as Wi-Fi or Wi-Fi Direct or any other wireless standard comprising optical, acoustical or conductive intracorporal principles. In this first configuration, implantable device 15 may communicate with other devices in system 10 by relaying communication through charging device 40. Charging device 40 may be in either wired or wireless communication with one or more of the devices in system 10 using one or more well-known communication standards including but not limited to GSM, LTE, CDMA, BLUETOOTH™, Bluetooth low energy, ZigBee and any IEEE 802.11 wireless standard such as Wi-Fi or Wi-Fi Direct. For example, charging device 40 may connect with implantable device 15 using Wi-Fi Direct and also may make a connection with a local Wi-Fi router and connect to the internet. Through the Internet, charging device 40 may be in communication with monitoring and control device 60, mobile device 80, and/or remote server 95.

Charging device 40, monitoring and control device 60 and mobile device 80 may each be configured to run instructions stored on a non-transitory computer readable medium programmed with messaging protocols that allows each device to communicate to one another over the internet. Commands may be communicated to microprocessor 41 of charging device 40 from monitoring and control device 60 and/or mobile device 80 which may subsequently be relayed from charging device 40 to implantable device 15. In this manner, communicating with charging device 40 through the monitoring and control device 60, a clinician may communicate with implantable device 15 to set or adjust the operational parameters of implantable device 15. Upon receiving the command to set or adjust the operational parameters, implantable device 15 will set or adjust the operational parameters according to the instructions from charging device 40. Alternatively, charging device 40 may communicate with other devices within system 10 using different communication standards discussed above.

Where charging device 40 is used as a relay point between implantable device 15 and other devices of system 10, information such as physiological and/or operational data may be communicated from implantable device 15 to charging device 40 and then from charging device 40 to remote server 95 for storage on remote server 95. For example, implantable device 15 may transmit physiological and/or operational data to charging device 40. Charging device 40 may store the physiological and/or operational data and may run a programmed routine configured to transmit the stored physiological and/or operational data to remote server 95 for remote storage. The programmed routine may include instructions that permit the charging device to communicate with remote server over the internet or via a wireless telephony regime. The instructions also may cause communications from charging device 40 to be encrypted such that transmission of physiological and/or operational data is encrypted. Alternatively, charging device 40 may transmit the physiological and/or operational data to monitoring and control device 60 and/or mobile device 80 to be stored on the respective devices. In this configuration, monitoring and control device 60 and/or mobile device 80 may run a programmed routine configured to transmit the stored physiological and/or operational data to remote server 95 for remote storage. The programmed routine further may cause monitoring and control device 60 and mobile device 80 to transmit operational parameters and instructions or commands to charging device 40 to be relayed to implantable device 15.

The second way in which implantable device 15 may communicate with system 10, is by directly communicating with one or more devices in system 10 without the use of a relay device. In this configuration, communication with other devices within system 10 may be established using any of the communication standards discussed above including close range standards, such as BLUETOOTH™, Bluetooth low energy, ZigBee and Wi-Fi, and long range standards such as GSM, LTE, CDMA. It is further understood that implantable device 15 may communicate with different devices within system 10 using different communication standards as implantable device 15 may be configured to communicate using more than one communication standard. Like in the first arrangement, where charging device 40 was used as a relay, clinician may communicate with implantable device 15 to set or adjust the operational parameters of implantable device 15. Upon receiving the command to set or adjust the operational parameters, implantable device 15 will set or adjust the operational parameters according to the instructions from charging device 40.

For example, implantable device 15 may be in direct wireless communication with monitoring and control device 60 using BLUETOOTH™ or Bluetooth low energy connectivity. Monitoring and control device 60 may include non-transitory computer readable medium programmed with instructions that, when run on monitoring and control device 60 allows monitoring and control device 60 to directly communicate with implantable device 15. In this example, during patient visits, a clinician using monitoring and control device 60 may wirelessly connect to implantable device 15 to download for review, data generated by and stored on implantable device 15. Further, monitoring and control device 60 may transmit operational parameters to implantable device 15 to adjust or set operational parameters of implantable device 15 without using charging device 40 as a relay point. Where implantable device 15 includes a pump, a clinician may adjust operational parameters in the pump such as timing intervals for running the pump. Upon receiving the operational parameters, implantable device 15, e.g. the one or more processors, may adjust operation according to the received operational parameters. While in communication with implantable device 15, the clinician using monitoring and control device 60 also may download operational and/or physiological data stored on implantable device 15. In yet another example, implantable device 15 may support Wi-Fi connectivity and the clinician using monitoring and control device 60 may directly connect to implantable device 15 even when the clinician and patient are not in the same location.

Implantable device 15 also may be configured to communicate directly with mobile device 80 and/or remote server 95. Mobile device 80 and remote server 95 may each similarly include a non-transitory computer readable medium programmed with instructions that, when run on mobile device 80 and/or remote server 95 allow mobile device 80 and/or remote server 95, respectively, to directly communicate with implantable device 15. In this configuration, implantable device 15 may transmit data generated from the sensors incorporated in implantable device 15 to remote server 95 so that the sensor data is accessible for review by the data analyst device 100. Mobile device 80 and/or remote server 95 may communicate with implantable device 15 using any of the well-known methods discussed above. For example mobile device 80 and remote server 95 may have Wi-Fi compatibility and communicate with implantable device 20 via the internet. Alternatively, or in addition to, implantable device 20 may be configured to have wireless telephony capabilities and establish a connection to mobile device 80, for example, using LTE.

Whether implantable device 15 uses charging device 40 to communicate with system 10 or is in direct communication with other devices within system 10, monitoring and control device 60 and/or mobile device 80 may each have non-transitory computer readable medium and may each run instructions on the non-transitory computer readable medium to cause the monitoring and control device 60 and/or mobile device 80 to communicate with the remote server and receive from the remote server operational and/or physiological data. Specifically, monitoring and control device 60 and/or mobile device 80 may interrogate remote server 95 for new data uploaded onto remote server 95, including data generated by implantable device 15 and data generated by data analyst device 100, discussed in more detail below. For example, monitoring and control device 60 and/or mobile device 80 may be configured to manually interrogate remote server 95 to determine if analyst data has been uploaded to remote server 95.

Alternatively, monitoring and control device 60 and/or mobile device 80 may each include a non-transitory computer readable medium programmed with instructions that, when run on monitoring and control device 60 and/or mobile device 80, cause monitoring and control device 60 or mobile device 80, respectively, to automatically periodically interrogate remote server 95 for new analyst data uploaded to remote server 95 to determine, for example, whether uploaded analyst data includes a diagnosis of a medical condition and/or an indication of a high risk of a medical condition. Monitoring and control device 60 may be configured to transmit an alert to mobile device 80 upon confirmation that the analyst data includes a diagnosis of a medical condition and/or an indication of high risk of a medical condition. Data analyst device 100 and implantable device 15 also may be configured to automatically generate and transmit an alert to monitoring and control device 60 and/or mobile device 80 indicating that data has been transmitted to the server. Preferably communication between implantable device 15, charging device 40, monitoring and control device 60, mobile device 80, remote server 95 and/or data analyst device 100 is encrypted.

Figure 6:
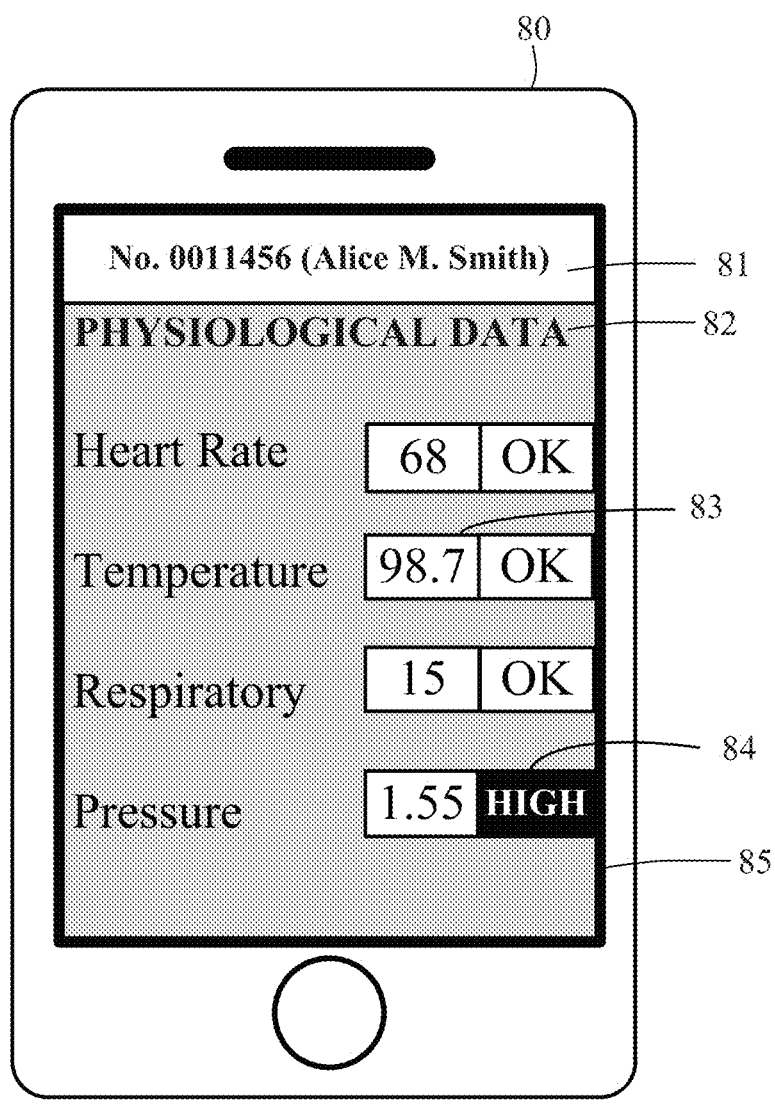
FIG. 6 illustrates an exemplary embodiment of a mobile graphic user interface displayed on the mobile device.

Referring now to FIG. 6, mobile device 80 may include a non-transitory computer readable medium programmed with instructions that, when run, permit mobile device 80 to view data generated by implantable device 15. As shown in FIG. 6, mobile device 80 may be configured to run mobile graphic user interface 85 for displaying patient identifying information 81 and patient data 82 such as physiological and/or operational data. In this manner, the patient using the patient mobile device 80 may view instantaneous or archived data generated by implantable device 15, allowing the patient to monitor his or her physiological wellbeing at all times. Specifically, mobile graphic user interface 85 may display data 83 generated by one or more sensors integrated into implantable device 15. For example, mobile graphic user interface 85 may display temperature data as well as heart rate, heart rate variation, physical activity, respiratory and pressure data generated by the plurality of sensors.

Mobile graphic user interface 85 also may output parameter status 84. Parameter status 84 may indicate the status of the measured parameter, e.g., whether the measured parameter is LOW, HIGH or OK (normal) for a given patient. For example, parameter status 84 may indicate to the patient how the measured parameter compares to pre-programmed thresholds. If the pressure reading exceeds a pre-programmed threshold, the parameter status will read "HIGH". Similarly, if the pressure reading is below a pre-programmed threshold, the parameter status will read "LOW". The other parameter statuses in FIG. 6 read "OK" indicating that those measurements fall within a normal range between thresholds.

The data displayed on mobile graphic user interface 85 may be received from remote server 95 when mobile device 80 has established a connection with remote server 95. Alternatively, when mobile device 80 has established a direct connection with implantable device 15, the data displayed on graphic user interface 85 may be transmitted directly from implantable device 15. In yet another example, the data displayed on graphic user interface 85 may be transmitted from charging device 60. The status parameters illustrated in FIG. 6 may be determined by software run on mobile device 80 or may be included in the data received by mobile device 80.

Figure 7:
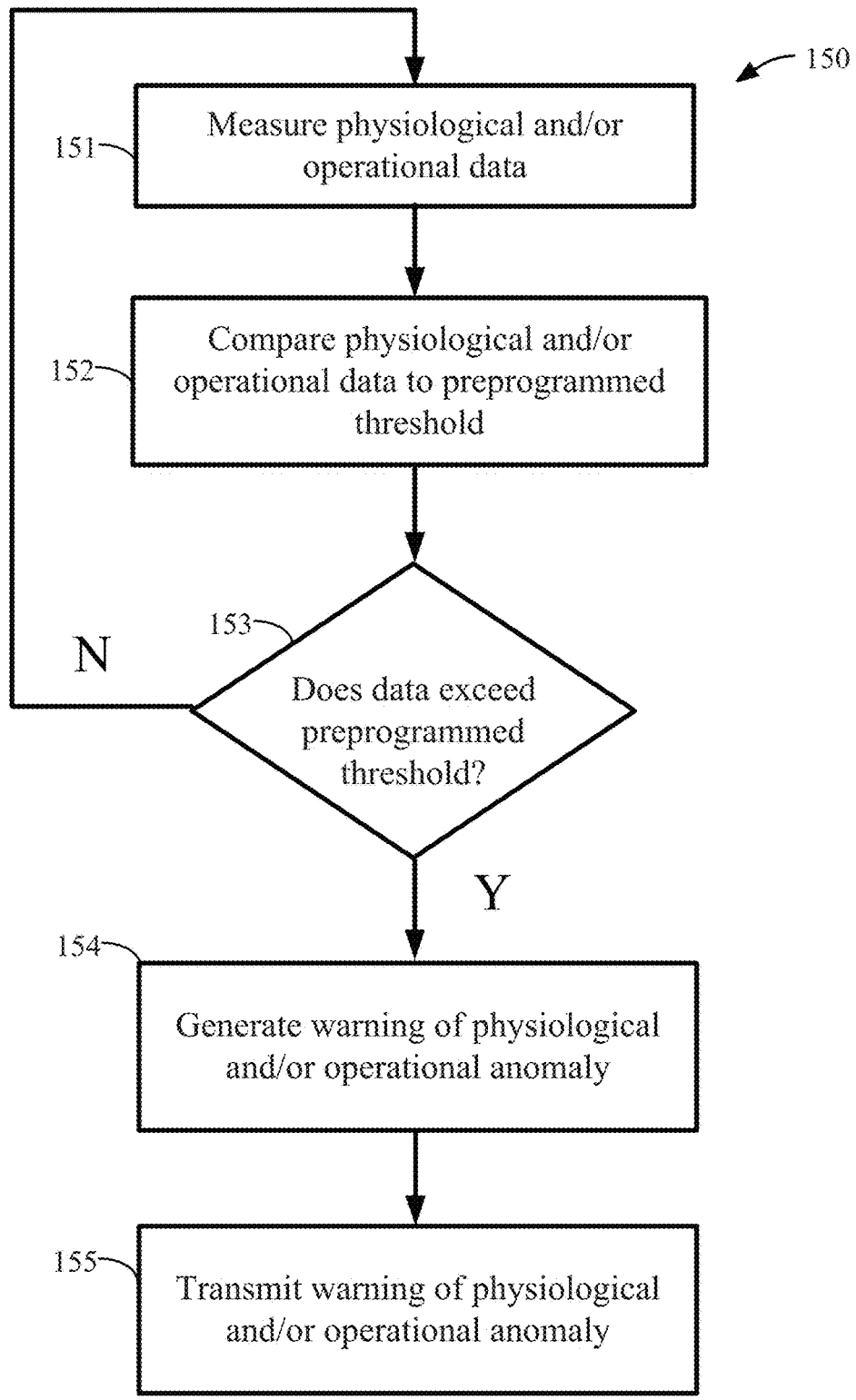
FIG. 7 illustrates a flow chart outlining an exemplary process for generating and transmitting a warning of a physiological and/or operational anomaly.

Referring now to FIG. 7, an exemplary test protocol is illustrated, which is run by implantable device 15 to compare measured data to preprogrammed thresholds to determine if a warning should be generated. Test protocol 150 begins with measuring step 151 where the processor of implantable device 15 directs at least one of the sensors in implantable device 20 to measure physiological and/or operational data. Subsequently, in comparison step 152, the processor executes instructions to compare the measured data to preprogrammed thresholds. The preprogrammed thresholds may be set or updated from operational instructions transmitted to implantable device 15 from other devices within system 10. At decision 153, if the measured physiological and/or operational data is consistent with the preprogrammed threshold range, the implantable device is instructed to once again measure physiological or operational data after waiting a predetermined period of time. If, however, the measured data is outside the preprogrammed threshold range, at warning step 154, the processor executes instructions directing implantable device 15 to generate a warning message. Upon generation of a warning message, transmission step 155 executes instructions directing implantable device 15 to transmit the warning to at least one or more of mobile device 80, monitoring and control device 60, charging device 40 and remote server 95.

Figure 8:
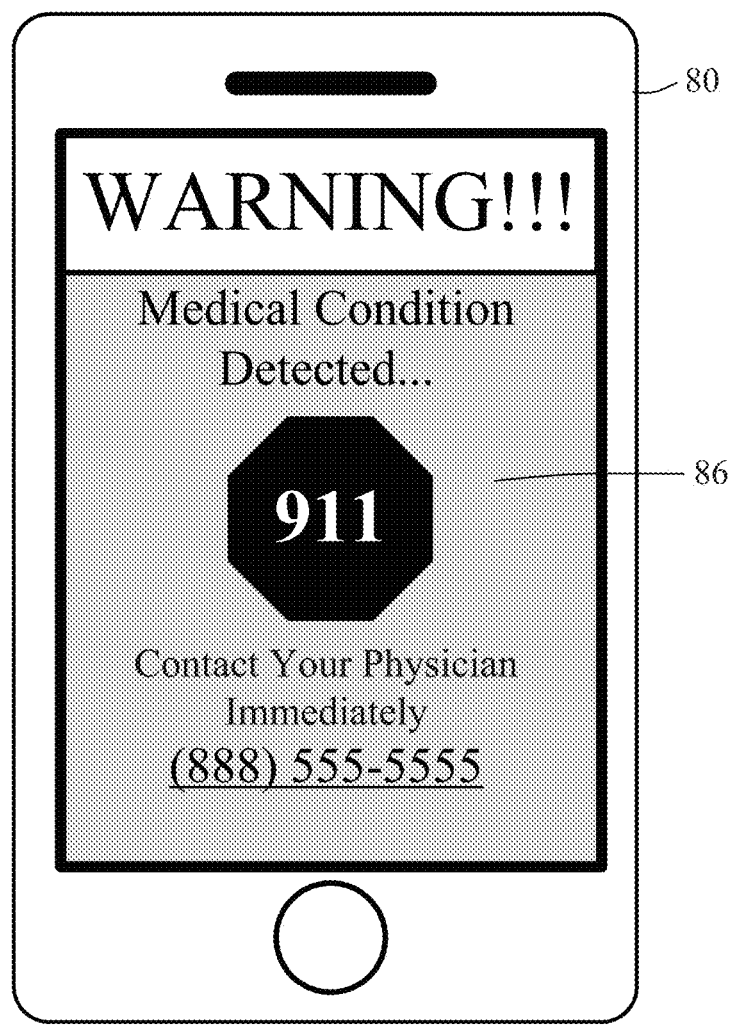
FIG. 8 illustrates an exemplary embodiment of a warning graphic user interface displayed on the mobile device.

Referring now to FIG. 8, mobile device 80 is shown running instructions stored on a non-transitory computer readable medium that, when run on mobile device 80, causes the mobile device to communicate a warning message to the patient/caregiver. As explained above and shown in FIG. 7, the warning message may be generated by implantable device 15 and transmitted either directly from implantable device 15 or relayed through charging device 40. Alternatively, the warning may be generated by the data analyst using data analyst device 100 or monitoring and control device 60 where analysis of the data by the data analyst or clinician revealed a problem or otherwise raised concern. Alternatively, mobile device 80 may analyze physiological and/or operational data by comparing the physiological and/or operational data to preprogrammed thresholds and/or input physiological and/or operational data into preprogrammed algorithms and may generate a warning message if necessary, e.g., above or below programmed thresholds and/or outside a programmed threshold range.

Warning graphic user interface 86 may show actionable insight related to the measured physiological and/or operational data and may show a warning message related to the physiological and/or operational data. Warning graphic user interface 86 may indicate that an anomaly has been detected or may even display the measured parameter compared to the predetermined threshold. For example, analysis from implantable device 15 may detect an irregular heartbeat and upon detection, warning graphic user interface 86 may alert the patient to this anomaly. Warning graphic user interface 86 may further include a direct link to the patient's physician, either by text, email or phone. If it is possible to alleviate the condition by adjusting operational parameters, warning graphic user interface 86 may seek permission from the patient to adjust the operational parameters. Where the warning is issued by data analyst device 100 the warning message also may indicate the type of medical condition that has been detected and/or other actionable insight generated. Warning graphic user interface 86 may further include a link to the data related to the warning and/or analysis of the data. Emergency responders may simultaneously be contacted and informed of the patient's location and condition upon generation of the warning message.

Where the warning is generated by implantable device 15, mobile device 80 and/or data analyst device 100, a physician or clinician using monitoring and control device 60 may also receive an alert on monitoring and control device 60 regarding the same information displayed on warning graphic user interface 86. The alert may further include data related to the warning, actionable insight and/or a link to access the data, similar to the warning shown in FIG. 9. Where the warning was generated by implantable device 15 or data analyst device 100, the physician may then review the parameters in question and if appropriate send the warning to mobile device 80.

If it is possible to alleviate the condition by adjusting operational parameters, a request may be sent to the physician or clinician to adjust operational parameters of implantable device 15, and upon receiving permission, command implantable device 15 to adjust operation, either by communicating the command directly from monitoring and control device 60 to the implantable device or relaying the command through the charging device. Upon receiving the command, implantable device 15 may adjust the operational parameter or parameters. For example, the command may direct the processor of implantable device 15 to pump more or less fluid from one body cavity, e.g. peritoneal, pleural, pericardial, to another body cavity, e.g., bladder, peritoneal cavity, and/or to adjust time intervals between pumping sessions. Implantable device 15 may send a similar alert to any number of devices within the system including data analyst device 100. An alert sent to data analyst device 100 from implantable device 15 may further include the most recent data measured by the implantable device relating to the warning being transmitted, allowing the remote analyst to immediately access and analyze the relevant data.

Figure 9:
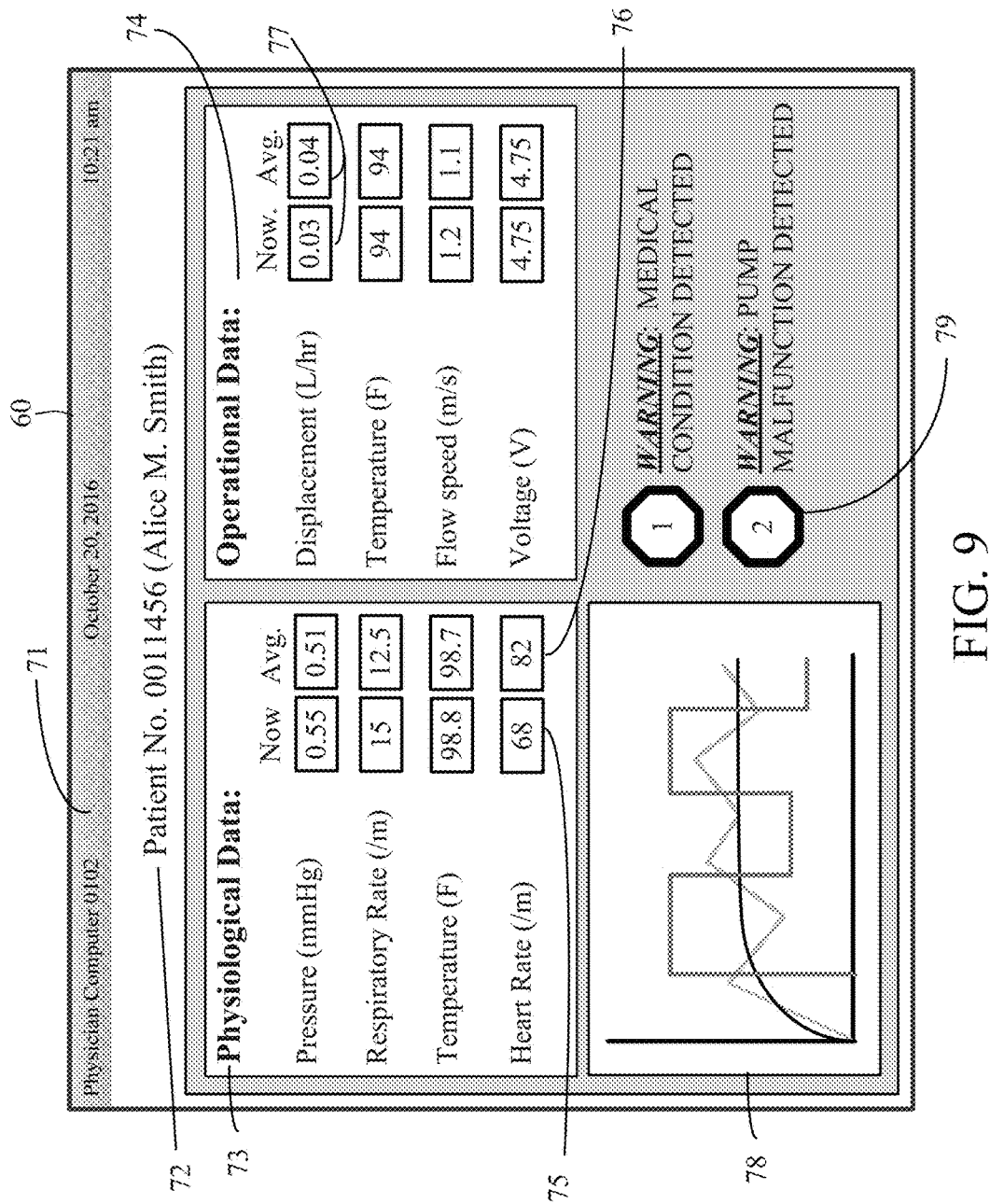
FIG. 9 illustrates an exemplary embodiment of the physician graphic user interface displayed on the monitoring and control device.

Referring now to FIG. 9, monitoring and control device 60 may run instructions stored on a non-transitory computer readable medium programmed to permit monitoring and control device 60 to retrieve and view data generated by implantable device 15 and/or data analyst device 100. The data received by monitoring and control device 60 on data analyst device 100 may provide a clinician or physician actionable insight, i.e. may provide the physician enough information to determine how to act or what measures to take to address a problem or concern. As shown in FIG. 9, graphic user interface 61 provides a user friendly view of the data and permits a clinician to receive relevant information in a short period of time. As explained above, monitoring and control device 60 may receive this data from implantable device 15, charging device 40, mobile device 80, remote server 95 and/or data analyst device 100.

Clinician graphic user interface 71 shown in FIG. 9 is illustrative of an exemplary clinician graphic user interface. As shown in FIG. 9, clinician graphic user interface 61 may include patient identifier 72 which may include a record locator such as a patient number and/or the patient's name. Clinician graphic user interface 60 may, for example, display data arranged into physiological data box 73 and operational data box 74. Physiological data box 63 may include current physiological measurements 75 generated by implantable device 15 as well as average and/or prior measurements 76 archived by implantable device 15, remote server 95, charging device 40 and/or monitoring and control device 60. For example, physiological data box 73 may display physiological parameters such as the current respiratory rate, current pressure of a body cavity, current temperature of a body cavity or targeted region of a body, current heart rate, or any other current measurement sensed by implantable device 15 indicating the physiological state of the body. Physiological box 73 may also display the physiological parameters such as average respiratory rate, the average pressure of a body cavity, the average temperature of a body cavity or targeted region of a body, the average heart rate, heart rate variability over a period of time or any other average measurement sensed by implantable device 15 indicating the physiological state of the body, as well as one or more previously measured respiratory rates, previously measured pressures of a body cavity, previously measured temperatures of a body cavity or targeted region of a body, previously measured heart rate or any other previously measured parameter sensed by implantable device 15. Illustratively, the current pressure may be 0.55 mmHg while the average pressure may be 0.51 mmHg, the current respiratory rate may be 15 breathes per minute while the average is 12.5, the current temperature may be 98.8 while the average temperature may be 98.7 and the current heart rate may be 68 beats per minute while the average heart rate may be 82 beats per minute.

Similarly, operational data box 74 may display operational data such as operational measurements 77 which may include displacement, temperature, duration and voltage measurements or any other measurements related to performance of the implantable pump 15 or performance of hardware incorporated into the implantable pump. Operational data box 74, like physiological data box 73, may show current operational measurements of implantable device 15 or measurements archived by implantable device 15, remote server 95, charging device 40 and/or monitoring and control device 60. For example, operational data box 74 may show operational parameters such as the current measurements for the hardware in implantable device 15, e.g., current displacement of an incorporated pump, current temperature of a battery, current flow speed, current voltage measurements, or any other current measurement sensed by implantable device 15 indicative of the operation of implantable device 15 or hardware incorporated in implantable device 15.

Operational box 74 also or alternatively may show operational parameters such as average displacement or a previously recorded displacement measurements, average temperature or a previously recorded temperature measurements, average flow speed or a previously recorded flow speed measurements, average voltage or a previously recorded voltage measurements or any other average or previously recorded measurement sensed by implantable device 15 indicative of the operation of implantable device 15 or hardware incorporated in implantable device 15. Operational data box 74 may further include operational data measurements such as battery and/or pump temperature, pump RPMs, humidity within the housing of implantable device 15, or any other measurements related to the performance or operation of implantable device 15 or hardware incorporated into implantable device 15.

Clinician graphic user interface 71 may also show other parameters and data amounting to actionable insight. For example, clinician graphic user interface 71 may include parameters calculated from measured physiological and/or operational parameters such as viscosity of a fluid within a body cavity or burn rate of calories. Actionable insight garnered from measured physiological and/or operational parameters may be generated using algorithms programmed into implantable device 15, monitoring and control device 60, mobile device 80, or data analyst device 100. Alternatively, or in addition to, a data analyst may analyze measured physiological and/or operational parameters on data analyst device 100 and generate actionable insight by comparing data to known trends or correlations.

Using clinician graphic user interface 71, a clinician or physician may adjust the performance of implantable device 15 by altering operational settings which may also appear in operational data box 74. For example, a clinician may change the desired displacement of the pump to 0.05. This change may be immediately communicated to implantable device 15 either through direct communication between implantable device 15 and monitoring and control device 60 or by using charging device 40 as a relay. Other examples of settings that a clinician or physician may adjust include the timing of pump activation, duration of pumping, or any other setting that may control the operation of implantable device 15 or hardware incorporated into implantable device 15.

Physician graphic user interface 71 may be customizable such that the physician may decide which data to display. The physician may choose to display any combination of archived data and current data. For example, the physician may customize the graphic user interface to display pressure averages over a period of time, e.g., the last six months, or may choose to display pressure highs and lows instead. Alternatively, a physician may customize the graphic user interface to only show select physiological and/or operational data but not others, e.g., the pressure, temperature and heart rate, but not the respiratory rate.

Clinician graphic user interface 71 also may generate one or more graphic representations of the data generated by implantable device 15. Graphic representation 78 may be generated by the physician to analyze a given parameter over a certain period of time. Graphic presentation 78 may include a flow chart(s), a pie chart(s), a bar graph(s), etc., representing measured physiological and/or operational data. The physician may choose to compare the patient's respiratory rate against the patient's heart rate for a given period of time to better understand the patient's oxygen saturation levels. As is discussed in more detail below, graphical analysis also may be generated by a dedicated analyst remotely and may be viewed by the clinician on graphic user interface 71. Similarly, tables and various other well-known data comparison methods may be generated remotely by dedicated analysts at data analyst devices and accessed by the clinician using graphic user interface 71. Clinician graphic user interface 71 may display additional information such as that shown in U.S. Pat. No. 9,039,652 to Degen, the entire contents of which are incorporated herein by reference.

Clinician graphic user interface 71 also may communicate various messages such as warnings 79 to the physician. Warnings or alerts may be generated by implantable device 15, mobile device 80 and/or data analyst device 100. For example, where implantable device 15 has a pump, clinician graphic user interface 71 may display a warning that the pump experienced a malfunction such as a clog and may even suggest methods for fixing the problem such as reversing flow direction. In another example, monitoring and control device 60 may run instructions stored on a non-transitory computer readable medium programmed to automatically compare physiological parameters and/or operational parameters against predetermined thresholds and to automatically generate a warning when an anomaly is discovered, e.g. when the measured parameters are above or below predetermined thresholds and/or are outside of a predetermined threshold range(s), much like the process shown in steps 152 to 155 in FIG. 7.

Clinician graphic user interface 71 may support a messaging protocol established on monitoring and control device 60 and/or mobile device 80. The messaging protocol may permit a physician or clinician to communicate a message and/or a warning to the patient by transmitting the message and/or warning to mobile device 80. For example, a physician may notice an unusual physiological and/or operational parameter or trend and may send a message to mobile device 80 to, for example, ask the patient how he or she feels or if he or she is experiencing certain symptoms or discomfort. Using the messaging protocol, the patient may inform the physician of his current condition using mobile device 80. If the physician instead notices from the physiological data that the patient is currently experiencing a medical event or is about to experience a medical event, the physician may immediately message the patient with instructions on what to do next. For example, the message may direct the patient to immediately cease all physical activity. Alternatively or additionally, the physician may message emergency services using clinician graphic user interface 71 and inform emergency services of the patient's location and condition.

Figure 10:
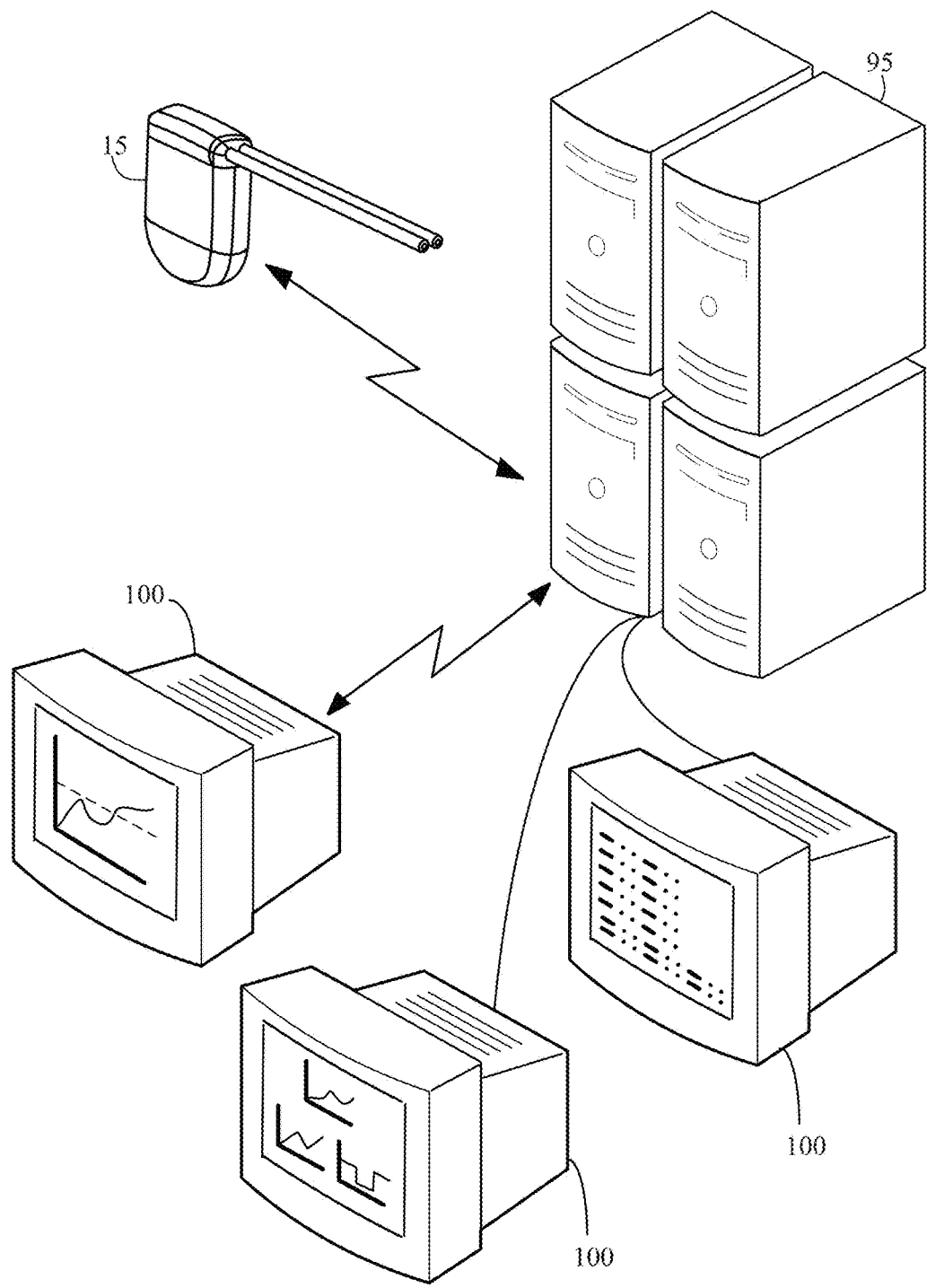
FIG. 10 illustrates an exemplary embodiment of a communication network established by a monitoring and control device, a remote server and a data analyst devices.

Referring now to FIG. 10, implantable device 15 optionally may be in direct wireless communication with remote server 95 via a LAN or WAN or communicate with remote server 95 additionally via charging device 40. Remote server 95 is also in communication with one or more data analyst devices 100 via a hard connection or wireless connection. One or more data analyst devices 100 also may be in communication with one another either wirelessly or by wired connection. An analyst using data analyst device 100 may periodically access, download and review on data analyst device 100, operational and/or physiological data received by remote server 95. Though data analyst device 100 may be in a different city or even a different country than implantable device 15, the analyst may access recently generated data from implantable device 15 via the remote server. In addition to receiving and accessing data from remote server 95, data analyst device 100 may transmit analyst data to remote server 95. Remote server 95 may store the data transmitted from data analyst devices 100 for retrieval by other devices such as mobile device 80 and/or monitoring and control device 60.

Data analyst device 100 also may establish a connection with other devices within the system and retrieve physiological and/or operational data for the other devices. For example, a remote analyst using data analyst device 100 may retrieve physiological data from implantable device 15, analyze the received physiological data, and transmit data analysis to a remote server 95 for download by other devices in the system. As another example, a remote analyst using data analyst device 100 may retrieve operational data from implantable device 15, analyze the received operational data, and transmit data analysis to a remote server 95 for download by other devices in the system. As explained above, the data analysis may include actionable insight that may provide a patient, caretaker, physician or clinician enough information to determine how to act or what measures to take to address a problem or concern.

Figure 11:
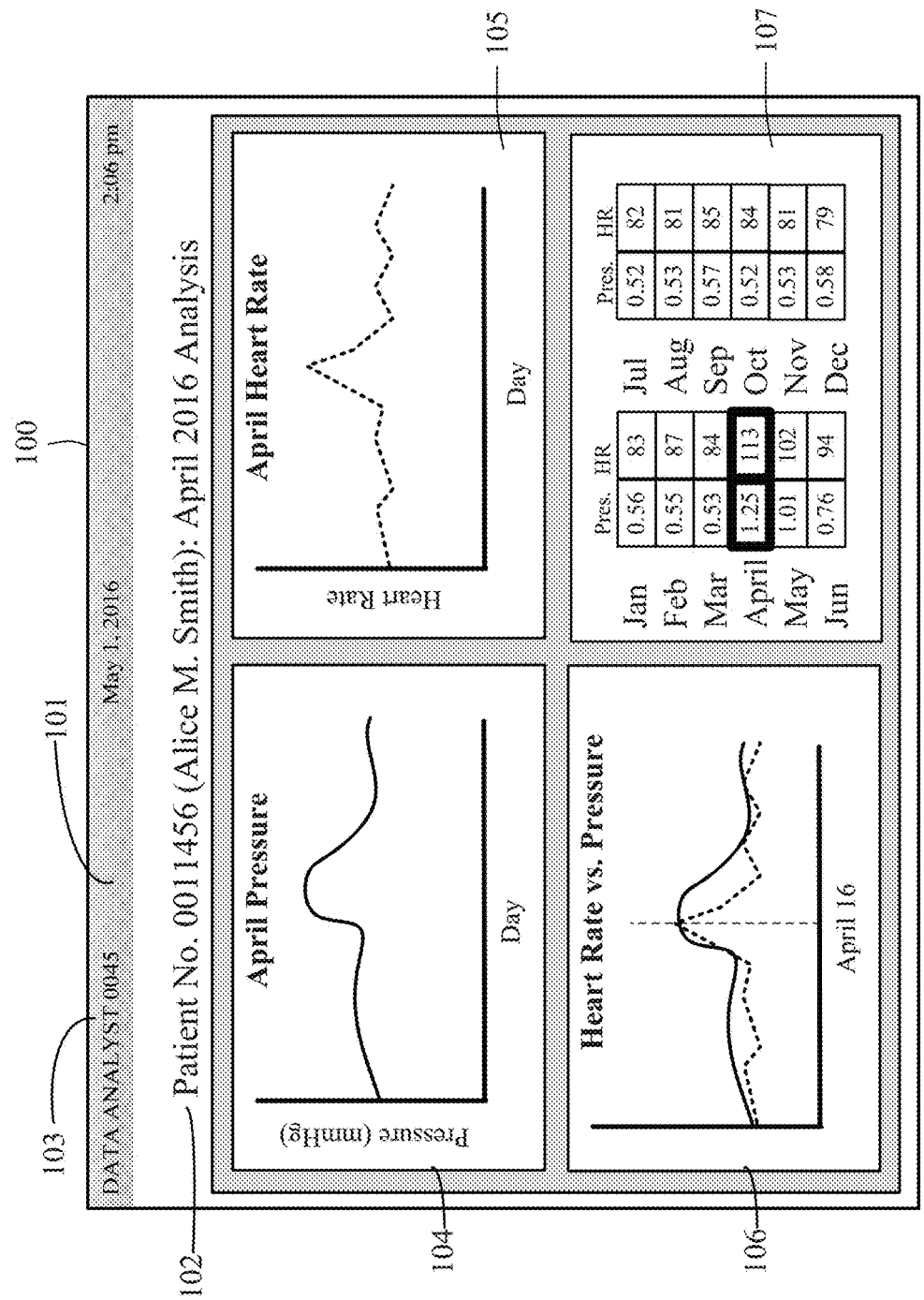
FIG. 11 illustrates an exemplary embodiment of an analyst graphic user interface displayed on the data analyst device.

Referring now to FIG. 11, analyst graphic user interface 101 is shown displayed on data analyst device 95. Analyst graphic user interface 101 may include patient identifier 102 which may include a record locator such as a patient identification number and/or the patient's name. Analyst graphic user interface 101 also may include data analyst identifier 103 that indicates the data analyst that generated the analysis. Analyst graphic user interface 101 is used to present the data analyst with an easy to understand representation of select data generated by implantable device 15 such as operational and/or physiological data. Analyst graphic user interface 101 may be completely customizable by the analyst to meet the analyst's needs and analytical approach. For example, analyst graphic user interface 101 may display data in a table format and/or a graphical format or in any other well-known format known for data analysis.

Using analyst graphic user interface 101, data analyst may review and analyze data, e.g., operational and/or physiological data generated by implantable device 15. Analyst also may use both current data and archived data to observe trends, predict trends, identify a medical condition and/or risk of a medical condition and produce actionable insight. Data from multiple patients may be anonymously or non-anonymously compared against each other. For example, data generated from a son's implantable device may be compared to data generated by a father's implantable device to better understand the effects of a hereditary condition where both patients have the same diagnosis. Alternatively, data from multiple patients known to have developed the same condition may be collectively analyzed to search for a trend among the data. Such a trend may help prevent or diagnose the medical condition in others who share the same trend.

In an exemplary embodiment, a data analyst may detect early warning signs of a heart attack by analyzing data generated by respiratory rate sensors, heart rate sensors, ECG sensors, blood pressure sensors, and/or temperature sensors. The data generated from these sensors may be compared to trends of individuals who have had heart attacks to determine whether a heart attack is imminent or likely. Similarly, using sensors including respiratory rate sensors, heart rate sensors, blood pressure sensors and/or temperature sensors, a data analyst may detect early signs of heart failure.

Specifically, from the respiratory rate sensor, shortness of breath may be detected in addition to chronic coughing or wheezing; from the blood pressure sensor, high blood pressure may be detected; from the temperature sensor, abnormalities in the patient's temperature may be detected; and from the heart rate sensor, an increased heart rate may be detected. Additionally, a third heart sound known as ventricular gallop or a protodiastolic gallop may also be detected which is an additional indicator of heart failure. Data analyst device 100 may run instructions stored on a non-transitory computer readable medium programmed to automatically compare data generated by implantable device 15 to various trends to determine the risk of a given condition or medical event. If a risk of a medical condition or event is determined to be high, the instructions may also generate a warning of the risk and automatically store the warning on remote server 95 for retrieval by mobile device 80 and/or monitoring and control device 60 and/or may automatically transmit the warning to mobile device 80 and/or monitoring and control device 60.

Analyst graphic user interface 101 shown in FIG. 11 is a snapshot illustrating an exemplary embodiment of an analyst's graphic user interface. As shown, analyst graphic user interface 101 may simultaneously display multiple graphical representations of data for comparison. For example, analyst graphic user interface 101 may display graphical representations of a measured pressure 104, over a period of time. Similarly, graphic user interface 101 also may display a graphical representation of the measured heart rate 105 over the same period of time. By comparing the measured pressure and the measured heart rate on overlaid graphical representation 106, an analyst may make immediate inferences and conclusions about the relationship between the two parameters. In this example, it is clear from the overlaid graphical representation that the measured pressure and measured heart rate spiked on the same day, April 16$^{th}$.

Analyst also may wish to compare certain data to archived data by generating a table. One or more tables may display one or more measured parameters from implantable device 15 over time including select measurements such as highs or lows over a time period. For example, table 107 illustrates the highest pressure measurement and the highest heart rate measurement for each month. In the snapshot shown, for the month of April, the highest pressure measured is 1.25 mmHg and the highest heart rate measured is 113 beats per minute. Analyst graphic user interface 101, arranged in the manner shown, allows the analyst to compare table 107 to graphic representations 104, 105 and 106. It is understood that an analyst may use any number of analytic tools that are well known in the art for analyzing the data generated by the implantable device.

The data analysis generated by data analyst device 100 may be formatted in any number of well-known ways and transmitted to and stored on remote server 95. For example, the results may be in the form of a report or a spreadsheet. Alternatively, the analyst may simply save the graphical representations or tables generated on data analyst device 100 to remote server 95. As explained above, in addition to transmitting the data analysis to remote server 95, a data analyst using analyst device 100 may transmit the results directly to mobile device 80 and monitoring and control device 60 and may generate an alert and communicate the alert to monitoring and control device 60 and/or mobile device 80 when data has been uploaded to remote server 95.

As discussed above and in accordance with the present disclosure, communication between devices in system 10 may be facilitated by a number of well-known techniques. While all devices within system 10 may be in communication with one another, it is understood that some devices may be in communication with less than the number of total devices in the system. For example, some devices of system 10 may be connected to the internet and others may make one-to-one connections to other devices that are connected to the internet using one or more of the well-known methods.

While various illustrative embodiments of the invention are described above, it will be apparent to one skilled in the art that various changes and modifications may be made therein without departing from the invention. For example, system 10 shown in FIG. 1 may include fewer components than those shown in FIG. 1 or may alternatively include more components such as more than one monitoring and control device or even more than one implantable device. The appended claims are intended to cover all such changes and modifications that fall within the true spirit and scope of the invention.

What is claimed:

1. A system for managing and reviewing data obtained from an implantable device at a data analyst device, the system comprising:

an outlet catheter configured to be implanted in a patient so as to be in fluidic communication with a patient's bladder;

an implantable device comprising a housing containing a first inductive charging circuit, a first microprocessor, a battery, a first communication unit, a pump coupled to the outlet catheter and configured to move fluid from a peritoneal cavity to the bladder via the outlet catheter, and a plurality of sensors, the implantable device configured to generate operational data and physiological data, the physiological data corresponding to the patient;

a charging device comprising a second inductive charging circuit, a second microprocessor, and a second communication unit, the charging device configured to wirelessly transfer energy transcutaneously from the second inductive circuit to the first inductive circuit to charge the battery, the charging device programmed to communicate with the implantable device to receive the operational data and the physiological data from the implantable device and to store the operational data and the physiological data on the charging device;

first instructions stored on a first non-transitory computer readable medium of the charging device configured to cause transmission of the operational data associated with the pump and the physiological data based on measurements from at least one sensor of the plurality of sensors associated with the pump stored on the charging device to a remote server so that the operational data and the physiological data are accessible from the remote server by a data analyst device; and second instructions stored on a second non-transitory computer readable medium of the data analyst device configured to cause the data analyst device to access the physiological data based on the measurements from the at least one sensor associated with the pump from the remote server, automatically compare the physiological data to other physiological data corresponding to at least one patient different from the patient, determine whether the physiological data exceeds one or more preprogrammed thresholds, and automatically generate an alert for transmission if the physiological data exceeds the one or more preprogrammed thresholds.

2. The system of claim 1, wherein the first instructions stored on the first non-transitory computer readable medium of the charging device are configured to cause the charging device to communicate with the remoter server via the Internet.

3. The system of claim 1, wherein the first instructions stored on the first non-transitory computer readable medium of the charging device are configured to cause the charging device to communicate with the remoter server via a wireless telephony regime.

4. The system of claim 1, wherein the first instructions stored on the first non-transitory computer readable medium of the charging device are also configured to cause transmission of operational instructions, including at least operational parameters, to the implantable device.

5. The system of claim 1, wherein the first instructions stored on the first non-transitory computer readable medium of the charging device are configured to encrypt communications between the charging device and the remote server such that transmission of the operational data and the physiological data is encrypted.

6. The system of claim 1, further comprising third instructions stored on a third non-transitory computer readable medium of a clinician computer configured to cause the clinician computer to communicate with the remote server and to receive from the remote server the operational data associated with the pump and the physiological data based on the measurements from at least one sensor of the plurality of sensors associated with the pump.

7. The system of claim 1, further comprising third instructions stored on a third non-transitory computer readable medium of a patient mobile communication device configured to cause the patient mobile communication device to communicate with the remote server and to receive from the remote server the operational data associated with the pump and the physiological data based on measurements from at the least one sensor of the plurality of sensors associated with the pump.

8. The system of claim 1, further comprising third instructions stored on a third non-transitory computer readable medium of a clinician computer configured to cause transmission of operational instructions, including at least operational parameters, from the clinician computer to the charging device.

9. The system of claim 1, wherein the second instructions stored on the second non-transitory computer readable medium of the data analyst device are further configured to cause the data analyst device to compile the operational data and the physiological data, generate analyst data and transmit the analyst data to the remote server.

10. The system of claim 1, wherein the second instructions stored on the second non-transitory computer readable medium of the data analyst device will cause the data analyst device to generate a warning message when the operational data exceeds one or more preprogrammed thresholds and communicate the warning message to at least one or more of a patient mobile communication device and a clinician computer.

11. The system of claim 1, wherein the plurality of sensors comprises at least one or more of a heart rate sensor, an ECG sensor, a temperature sensor, or a respiratory sensor and the physiological data comprises at least one of a heart rate, ECG data, a temperature or a respiratory rate.

12. A method of managing an implantable device comprising:
    establishing a wireless connection between a clinician computer and an implantable device, the implantable device comprising a housing containing an inductive charging circuit, a microprocessor, a battery, a communication unit, a pump and one or more sensors;
    receiving operational parameters at the implantable device from the clinician computer;
    adjusting operation of the implantable device according to received operational parameters at the implantable device;
    pumping fluid from a peritoneal cavity to a bladder of a patient via the pump coupled to an outlet catheter;
    generating operational data and physiological data from the one or more sensors in the implantable device, the physiological data corresponding to the patient;
    transmitting the operational data associated with the pump and physiological data based on measurements from the one or more sensors associated with the pump to a remote server so that the operational data and physiological data are accessible for review on a data analyst device;
    automatically comparing, on the data analyst device, the physiological data based on the measurements from the one or more sensors associated with the pump to other physiological data corresponding to at least one patient different from the patient;
    determining whether the physiological data exceeds one or more predetermined thresholds; and
    automatically generating a warning for transmission if the physiological data exceeds the one or more predetermined thresholds.

13. The method of claim 12, further comprising:
    automatically comparing, at the data analyst device, the operational data to one or more predetermined threshold ranges; and
    automatically generating, at the data analyst device, an alert if the operational data is outside one or more of the predetermined threshold ranges.

14. The method of claim 13, further comprising transmitting the alert from the data analyst device to at least one or more of the remote server, a patient mobile communication device and the clinician computer.

15. The method of claim 12, further comprising:
    analyzing on the data analyst device, at least one of the operational data and physiological data accessed from the remote server;
    generating analyst data on the data analyst device based on the at least one of the operational data and physiological data; and
    transmitting the analyst data from the data analyst device to the remote server.

16. The method of claim 15, wherein the generating the analyst data on the data analyst device further comprises generating at least one of a diagnosis of a medical condition, actionable insight and an indication of a heightened risk of a medical condition.

17. The method of claim 15, further comprising accessing, using a clinician computer, the analyst data stored on the remote server.

18. The method of claim 16, further comprising periodically interrogating, by the clinician computer, the remote server to determine whether the analyst data comprises at least one of a diagnosis of a medical condition or an indication of high risk of a medical condition.

19. The method of claim 18, further comprising transmitting an alert to a patient mobile communication device, from the clinician computer, upon confirmation that the analyst data comprises at least one of a diagnosis of a medical condition, an indication of high risk of a medical condition or other actionable insight.

* * * * *